United States Patent [19]
Buxton et al.

[11] Patent Number: 5,756,338
[45] Date of Patent: May 26, 1998

[54] ASPERGILLUS NIGER VACUOLAR ASPARTYL PROTEASE

[75] Inventors: Frank Buxton, Muttenz; Gabor Jarai, Oberwil, both of Switzerland; Jacob Visser, Wageningen, Netherlands

[73] Assignee: Novartis Corporation, Summit, N.J.

[21] Appl. No.: 731,045

[22] Filed: Oct. 8, 1996

Related U.S. Application Data

[62] Division of Ser. No. 328,314, Oct. 24, 1994, Pat. No. 5,674,728.

[30] Foreign Application Priority Data

Nov. 3, 1993 [GB] United Kingdom ............ 93810764

[51] Int. Cl.$^6$ ................ C12N 9/62; C12N 15/57; C12N 15/63; C12N 15/80
[52] U.S. Cl. ................ 435/219; 435/254.3; 536/23.2
[58] Field of Search ................ 435/219, 254.3, 435/2; 536/23.2

[56] References Cited

U.S. PATENT DOCUMENTS

| | | | |
|---|---|---|---|
| 4,885,249 | 12/1989 | Buxton et al. | 435/172.3 |
| 5,252,726 | 10/1993 | Woldike et al. | 536/24.1 |
| 5,324,660 | 6/1994 | Gleeson et al. | 435/254.23 |

FOREIGN PATENT DOCUMENTS

| | | |
|---|---|---|
| 0184438 | 12/1985 | European Pat. Off. |
| 0213593 | 8/1986 | European Pat. Off. |
| 0278355 | 2/1988 | European Pat. Off. |
| 0353188 | 7/1988 | European Pat. Off. |
| 0421919 | 8/1990 | European Pat. Off. |
| 0439997 | 12/1990 | European Pat. Off. |
| WO86/00089 | 1/1986 | WIPO. |
| WO88/0706 | 9/1988 | WIPO. |
| WO90/00192 | 1/1990 | WIPO. |
| WO92/17595 | 10/1992 | WIPO. |

OTHER PUBLICATIONS

Jarai et al., Gene 145:171–178 (1994).
Lott, T.J., et al., Nucleic Acids Research, vol. 17, "Nucleotide sequence of the Candida albicans aspartyl protease gene", p. 1779, 1989.
Barthomeuf, C., et al., "Isolation and Purification of New Protease from Aspergillus niger LCF N° 9", Biotechnology Techniques, 2(1):29–34 (1988).
Barthomeuf, C., et al., Abstract 52956, "Properties of new Alkaline Proteinase from Aspergillus niger", Chemical Abstracts, 111:319 (1989).
Barthomeuf, C., et al., "Properties of a New Alkaline Proteinase from Aspergillus niger", Chem. Pharm. Bull., 37 (5):1333–1336 (1989).
Berka, R.M., et al., "Molecular Cloning and Deletion of the Gene Encoding Aspergillopepsin A from Aspergillus awamori", Gene, 86:153–162 (1990).
Bosmann, H.B., "Protein Catabolism—II. Identification of Neutral and Acidic Proteolytic Enzymes in Aspergillus niger", Biochim. Biophys. Acta 293:476–489 (1973).
Chopra, E., et al., "Influence of Various Nitrogen and Carbon Sources on the Production of Pectolytic, Cellulolytic and Proteolytic Enzymes by Aspergillus niger", Folin Microbiol., 30:117–125 (1985).
Degan, Florence D., et al., "Purification and Characterization of Two Serine Carboxypeptidases from Asperfillus niger and Their Use in C–Terminal Sequencing of Proteins and Peptide Synthesis", Applied & Environ. Microbiol., 58(7):2144–2152 (1992).
Dunn–Coleman, Nigel S., et al., "Commercial Levels of Chymosin Production by Aspergillus", Biotechnology, 9:976–981 (1991).
Durham, Don R., et al., "Novel Alkaline–and Heat–Stable Serine Proteases from Alkalophilic Bacillus sp. Strain GX6638", J. Bacteriology, 169(6):2762–2768 (1987).
Frederick, G.D. et al., "Distant Upstream Regulatory Sequences Control the Level of Expression of the am (GDH) Locus of Neurospora crassa", Curr. Genet., 18:53–58 (1990).
Frederick, G.D. et al., :"Cloning and Characterization of pepC, a Gene Encoding a Serine Protease from Aspergillus niger", Gene, 125:57–64 (1993).
Gunkel, F.A., et al., "Proteinase K from Tritirachium album Limber", Eur. J. Biochem., 179:185–194 (1989).
Habener, J.F., et al., "5–Fluorodeoxyuridine as an Alternative to the Synthesis of Mixed Hybridization Probes for the Detection of Specific Gene Sequences", PNAS, 85:1735–1739 (1988).
Ichishima, Eiji, "Purification and Characterization of a New Type of Acid Carboxypeptidase from Aspergillus", Biochim. Biophys. Acta, 258:274–288 (1972).
Inoue, Hideshi, et al., "The Gene and Deduced Protein Sequences of the Zymogen of Aspergillus nigger Acid Proteinase A", J. Biol. Chem., 266(29):19484–19489 (1991).
Isogai, Takao, et al., "Cloning and Nucleotide Sequences of the Complementary and Genomic DNAs for the Alkaline Protease from Acremonium Chrysogenum", Agric. Biol. Chem., 55(2):471–477 (1991).
Jany, K.–D. et al., "Amino Acid Sequence of Proteinase k from the Mold Tritirachium album Limber", Febs Letters, 199 (2):139–144 (1986).

(List continued on next page.)

Primary Examiner—Robert A. Wax
Assistant Examiner—William W. Moore
Attorney, Agent, or Firm—Gregory D. Ferraro

[57] ABSTRACT

The present invention concerns a novel DNA sequence coding for an Aspergillus aspartic protease, an Aspergillus aspartic protease per se and a method for the preparation thereof. The invention further concerns a novel Aspergillus mutant strain defective in a protease of the aspartic proteinase-type, which is useful for the expression of heterologous protein, and a method for the preparation of such a mutant strain.

3 Claims, No Drawings

OTHER PUBLICATIONS

Jaton–Ogay, K., et al., "Nucleotide Sequence of a Genomic and a cDNA Clone Encoding an Extracellular Alkaline Protease of *Aspergillus fumigatus*", *FEMS Microbiology Letters*, 92:163–168 (1992).

Krishnan, S., et al., "Purification of an Acid Protease and a Serine Carboxypeptidase from *Aspergillus niger* using Metal–chelate Affinity Chromatography", *J. of Chromatography*, 329:165–170 (1985).

Krishnan, Sivadasan et al., "Purification and Some Properties of Three Serine Carboxy–peptidases from *Aspergillus niger*", *J. of Chromatography*, 370:315–326 (1986).

Kumagai, I., et al, "Isolation, Purification and Some Chemical Properties of an Acid Carboxypeptidase from *Aspergillus niger var.* Macrosporus", *Biochim. Biophys. Acta*, 659:334–343 (1981).

Matsushima, K., et al., Abstract 63505w, "High Alkaline Protease–yielding Mutants of *Aspergillus niger* induced by Ultraviolet Irradiation", *Chemical Abstracts*, 73:13 (1967).

Mattern, I.E., et al., "Isolation and Characterization of Mutants of *Aspergillus niger* Deficient in Extra–Cellular Proteases", *Mol. Gen. Genet.*, 234:332–336 (1992).

Moehle, C.M., et al., "Protease B of the Lysosomelike Vacuole of the Yeast *Saccharomyces cerevisiae* Is Homologous to the Subtilisin Family of Serine Proteases", *Molecular and Cellular Biology*, 7(1): 4390–4399 (1987).

Monod, Michel et al., "Virulence of Alkaline Protease–Deficient Mutants of *Aspergillus fumigatus*", *FEMS Microbiology Letters*, 106:39–46 (1993).

Ogawa, Y., et al., "Secretion of *Aspergillus oryzae* Alkaline Protease in an Osmophilic Yeast, *Zygosaccharomyces rouxii*", *Agric. Biol. Chem.*, 54(10):2521–2529 (1990).

Ostoslavskaya V.I., et al., Abstract DBA Accession No. 86–12806, "The Primary Structure of Aspergillopepsin A, Aspartic Proteinase from *Aspergillus awamori*: IV. Amino Acid Sequence of the Enzyme–Aspartic Protease", *Biotechnology Abstracts* (1986).

Pourrat, H., et al., "Production of Semi–Alkaline Protease by *Aspergillus niger*", *J. Ferment. Technol.*, 66(4):383–388 (1988).

Sakka, K., et al., "Purification and Some Properties of Serine Proteinase from a Mutant of *Aspergillus niger*", *J. Ferment. Technol.*, 63(5):479–483 (1985).

Samai, B.B., et al., "Cloning and Expression of the Gene Encoding a Novel Proteinase from *Tritirachium album Limber*", *Gene*, 85:329–333 (1989).

Samai, B.B. et al., "Isolation and Characterization of the Gene Encoding a Novel, Thermostable Serine Proteinase from the Mould *Tritirachium album Limber*", *Molecular Microbiology*, 4(10):1789–1792 (1990).

Siezen, R.J., et al., "Homology Modelling and Protein Engineering Strategy of Subtilases, the Family of Subtilisin–like Serine Proteinases", *Protein Engineering*, 4(7):719–737 (1991).

Takahashi, K., et al., "The Primary Structure of *Aspergillus niger* Acid Proteinase A", *J. Biol. Chem.*, 266(29):19480–19483 (1991).

Tatsumi, H., et al., "Cloning and Sequencing of the Alkaline Protease cDNA from *Aspergillus oryzae*", *Agric. Biol. Chem.*, 52(7):1887–1888 (1988).

Tatsumi, H., et al., "A Full Length cDNA Clone for the Alkaline Protease from *Aspergillus oryzae*: Structural Analysis and Expression in *Saccharomyces cerevisiae*", *Mol. Gen. Genet.*, 219:33–38 (1989).

Tatsumi, H., et al., "Cloning and Expression in Yeast of a cDNA Clone Encoding *Aspergillus oryzae* Neutral Protease II, a Unique Metalloprotease", *Mol. Gen. Genet.*, 228:97–103 (1991).

Wolf, D.H., et al., "Studies on a Proteinase B Mutant of Yeast", *Eur. J. Biochem.*, 98:375–384 (1979).

Yelton, M.M. et al., "*Transformation of Aspergillus nidulans* by using a trpC Plasmid", *PNAS*, 81:1470–1474 (1984).

ASPERGILLUS NIGER VACUOLAR ASPARTYL PROTEASE

This is a divisional of Ser. No. 08/328,314, filed Oct. 24, 1994 which issued as U.S. Pat. No. 5,674,728 on Oct. 7, 1997.

BACKGROUND OF THE INVENTION

Aspergillus species, and in particular *Aspergillus niger*, are used for the industrial production of enzymes used in the food processing industry. *A. niger* has advantages as a host for the production of recombinant proteins because of its large capacity for secretion of proteins, and because systems are available for its molecular genetic manipulation. However, the presence of proteases in the culture fluid, periplasmic space or endoplasmic reticulum and Golgi apparatus has proven deleterious to the expression of heterologous proteins in *A. niger*, in fact Aspergilli are used commercially to produce proteases. A number of extracellular proteases from Aspergilli have been described in the literature. The gene pepA encoding aspergillopepsin A from *Aspergillus awamori* has recently been cloned. The pepA gene product accounts for a major part of the secreted acid proteases of *A. niger* and strains in which the pepA gene has been deleted have allowed increased expression of heterologous proteins in *A. niger* var. *awamori*. Other protease genes have also been recently cloned from Aspergilli and these include an alkaline aspartic protease of *A. oryzae*, an alkaline aspartic protease of *A. fumigatus*, a non-pepsin type acid protease from *A. niger* var. *macrosporus*, a metalloprotease called neutral protease II from *A. oryzae*, and two serine proteases from *A. niger*.

Isolated and mutated protease genes of *A. niger* can be used for gene disruption experiments, i.e. the preparation of mutant strains in which the corresponding natural gene is destroyed. For example, the pepA gene from *Aspergillus awamori* has been destroyed by gene disruption in order to prepare aspergillopepsin A deficient strains.

However, as mentioned above Aspergilli produce a large number of different proteases and, thus, there is a continuing need for Aspergillus strains deficient in other proteases for the industrial production of proteins. For this purpose there is also a need for other protease genes which can be used for the preparation of protease deficient strains by in vitro mutagenesis, e.g. gene disruption. Moreover, there is also a need for recombinant protease proteins which can be industrially applied for protein processing.

Another major constituent of the secreted protease activities in *A. niger* are aspartic proteases. Aspartic proteases have been cloned in a number of fungi, e.g. the vacuolar protein pep4 (=pepA) of *S. cerevisiae*, the secreted proteases of Candida, Mucor, Rhizopus, Cryphonectria and Penicillium species, and the secreted major acidic proteases of both *A. niger* and *A. oryzae*. Recently a vacuolar protein gene was isolated from *Neurospora crassa* and was shown to have considerable sequence homology to yeast pep4.

It is now found that Aspergillus also produces another aspartic protease homologous to the pepsins but showing almost no homology to the known aspergillopepsin. The present invention focuses on the new protease.

OBJECT OF THE INVENTION

It is an object of the present invention to provide a DNA molecule encoding an Aspergillus aspartic protease.

A further object is to provide recombinant Aspergillus aspartic protease and for this purpose also a transformed Aspergillus strain for the production thereof.

Another object is to provide an Aspergillus strain defective in a aspartic protease gene which strain can be used for a more efficient production of heterologous or homologous proteins.

SUMMARY OF THE INVENTION

The present invention concerns an Aspergillus aspartic protease. Such a protease is herein named "Aspergillus-aspartic proteinase". An "Aspergillus-aspartic proteinase" of the present invention is understood as (a) being derived from Aspergillus spec., (b) exhibiting protease activity due to a catalytic aspartic acid residue at the active site, and and (c) having sufficient amino acid sequence homology with known aspartic proteases for being grouped into the aspartic proteinase family. However, included within the meaning of the term Aspergillus-aspartic proteinase as used in the present invention are also fragments of such an enzyme which retain aspartic protease activity, however, the full length enzymes are preferred embodiments. It is understood that also fusion proteins containing an "Aspergillus-aspartic proteinase" of the invention attached to additional amino acids, peptides or proteins are part of the present invention.

In a preferred meaning, Aspergillus-aspartic proteinase describes a protease or active fragment derived from *Aspergillus niger*, more preferentially a protease or active fragment having the amino acid sequence or part of the sequence shown under SEQ ID NO. 1.

The present invention also concerns an isolated DNA sequence encoding an Aspergillus-aspartic proteinase of the present invention, and a hybrid vector for the cloning and multiplication of such a DNA sequence. The invention further concerns an expression hybrid vector for the production of an Aspergillus-aspartic proteinase comprising such a DNA sequence funtionally linked with regulatory regions suitable for the expression of an Aspergillus-aspartic proteinase gene in a suitable host cell. The invention also concerns transformed host cells capable of expressing Aspergillus-aspartic proteinase, for example an Aspergillus strain capable of overexpressing Aspergillus-aspartic proteinase due to an increased copy number of the gene after transformation.

The invention also concerns an Aspergillus strain deficient in an Aspergillus-aspartic proteinase gene and a method for the production thereof by means of a DNA sequence encoding Aspergillus-aspartic proteinase which is no longer capable of expressing functional protein due to mutagenesis, e.g. gene disruption.

Moreover, the present invention concerns methods for the preparation of a DNA sequence, hybrid vector, expression vector and Aspergillus-aspartic proteinase of the invention as well as methods for the expression of an Aspergillus strain deficient in an Aspergillus-aspartic proteinase gene and of a host strain overproducing Aspergillus-aspartic proteinase.

DETAILED DESCRIPTION OF THE INVENTION

DNA Encoding Aspergillus-aspartic Proteinase, Hybrid Vectors for Cloning and Expression The present invention concerns a DNA molecule comprising a DNA sequence encoding an Aspergillus-aspartic proteinase, preferably of *Aspergillus niger*. The DNA sequence may contain one or more introns as have DNA molecules isolatable from a genomic DNA library, e.g. as the pepE gene shown in SEQ ID NO. 1. However, the invention also concerns an intron-less variant of the DNA sequence, for example, such isolatable by cDNA cloning or after mutagenesis e.g. by applying PCR technology. Such intronless genes are in particular useful for expression in non-Aspergillus hosts, preferably in procaryotes or yeast.

The invention concerns preferably a DNA molecule comprising a DNA sequence coding for the *A. niger* aspartic protease PEPE having the amino acid sequence shown in SEQ ID NO. 1 or a fragment thereof retaining aspartic protease activity. A DNA sequence of the invention is preferably the coding region for mature PEPE protease shown in the nucleotide sequence with SEQ ID NO. 1. However, the invention also concerns degenerate DNA sequences coding for PEPE or a fragment thereof, i.e. sequences in which nucleotides are replaced without changing the encoded amino acid sequence. Such DNA sequences are useful, for example, due to differences in the preferred codon usage in different hosts or due to the presence of new recognition sites for restriction enzymes.

The invention concerns also a hybrid vector comprising as insert a DNA sequence encoding an Aspergillus-aspartic proteinase of the invention, preferably a preferred form thereof. Such a hybrid vector of the invention is useful for the propagation and multiplication of a DNA sequence of the invention. The invention also concerns an expression vector suitable for the production of an Aspergillus-aspartic proteinase of the invention, preferably of the preferred forms. Such an expression vector comprises an "expression cassette" in which a DNA sequence coding for an Aspergillus-aspartic proteinase is funtionally linked with regulatory regions suitable for the control of the expression of such a DNA sequence in a desired host cell.

A hybrid vector of the invention, including an expression vector, may be derived from any vector useful in the art of genetic engineering, such as from viruses, phages, cosmids, plasmids or chromosomal DNA, such as derivatives of SV40, Herpes-viruses, Papilloma viruses, Retroviruses, Baculovirus, phage λ, e.g. NM 989 or EMBL4, or phage M13, e.g. M13mp8, bacterial plasmids, e.g. pBR322, pUC18, or yeast plasmids, e.g. yeast 2μ plasmid, or a defective virus, phage or plasmid in the presence of a helper virus, phage or plasmid allowing replication of said defective virus, phage or plasmid, e.g. M13(+)KS vector in presence of e.g. M14K07 helper phage, or also chromosomal DNA, derived e.g. from filamentous fungi such as Aspergillus spec., e.g. *A. niger*, for example those provided by EP 184 438. Preferred are vectors for *S. cerevisiae* or filamentous fungi, more preferably for Aspergillus spec., even more preferably for *A. niger*.

A hybrid vector of the invention, including an expression vector, provides for replication of a desired DNA in a suitable host, either as an extrachromosomal element or by integration in the host chromosome. Several possible vector systems are available for integration and expression of the cloned DNA of the invention. In principle, all vectors which replicate and are stably maintained in the chosen host are suitable. Thus, the vector is selected depending on the host cells envisaged for transformation. In general, such host cells may be prokaryotic or eukaryotic microorganisms such as bacteria, fungi such as yeast, preferably *S. cerevisiae*, or as filamentous fungi, preferably Aspergillus spec., more preferably *A. niger*, or cells of higher eukaryotic origin such as vertebrate, for example mammalian, cells. Suitable host cells will be discussed in detail hereinbelow. A hybrid vector of the invention, including an expression vector, which is maintained as extrachromosomal element comprises an origin of replication (ori) or an autonomously replicating sequence (ARS), selectable marker sequences, and, optionally, additional restriction sites. A vector which is destinated for integration into a host chromosome needs not comprise an ori or ARS because it is replicated in the cell in connection with the chromosome.

An origin of replication or an autonomously replicating sequence (a DNA element which confers autonomously replicating capabilities to extrachromosomal elements) is provided either by construction of a vector including an exogeneous origin such as derived from Simian virus (SV40) or another viral source, or by the host cell chromosomal mechanisms.

A hybrid vector of the invention, including an expression vector, may also contain selective markers depending on the host which is to be transformed, selected and cloned. Any marker gene can be used which facilitates the selection of transformants due to the phenotypic expression of the marker. Suitable markers are particularly those expressing antibiotic resistance, e.g. against tetracycline or ampicillin, or, in the case of auxotrophic fungal mutants, genes which complement host lesions. Corresponding genes confer, for example, resistance to the antibiotic cycloheximide, or provide for prototrophy in an auxotrophic yeast, preferably *S. cerevisiae*, mutant, for example the ura3, leu2, his3 or trp1 gene. It is also possible to employ as markers structural genes which are associated with an autonomously replicating segment providing that the host to be transformed is auxotrophic for the product expressed by the marker.

Of particular importance in context with hybrid vectors, in particular expression vectors, for *A. niger* are marker genes which complement *A. niger* host lesions, such as the argB gene coding for the ornithine carbamoyl transferase, e.g. derived from *A. niger* or *A. nidulans* (EP 184 438), or *A. nidulans* DNA fragments homologous to the *N. crassa* pyr4 gene. Other suitable marker genes are described hereinafter in connection with the description of transformed hosts of the invention.

A hybrid vector of the invention suitable for the multiplication of DNA coding for Aspergillus-aspartic proteinase in *E. coli* is, for example, plasmid pPEPE described hereinafter in the accompanying examples.

The term "expression cassette" in context of an expression vector of the present invention means a DNA sequence capable of expressing Aspergillus-aspartic proteinase and comprises a promoter operatively linked with an Aspergillus-aspartic proteinase coding region and optionally one or more further regulatory elements of the group consisting of a signal sequence, a transcriptional terminator, a transcriptional enhancer, a ribosomal binding site, a sequence for the efficient RNA processing, a sequence coding for efficient protein processing, and a sequence coding for correct protein localisation. In an expression cassette according to the present invention an Aspergillus-aspartic proteinase coding region may be combined with homologous regulatory elements, i.e. such naturally linked therewith, or with heterologous regulatory elements, i.e. such derived from other genes.

A wide variety of promoter sequences may be employed, depending on the nature of the host cell. Promoters that are strong and at the same time well regulated are the most useful.

Examples for promoters are the procaryotic $\lambda P_L$, $\lambda P_R$, *E. coli* lac, trp, or tac promoters. Promoters suitable for expression in yeast, preferably *S. cerevisiae*, are TRP1-, ADH1-, ADHII-, PHO3-, PHO5-, GAL10-, or glycolytic promoters such as the promoter of the enolase, glyceraldehyde-3-phosphate dehydrogenase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or the PH05-GAPDH hybrid promoter (EP Appl. No. EP-A-213 593). Other examples for eukaryotic promoters are promoters derived from eukaryotic viruses, e.g. SV40, Rous sarcoma virus, adenovirus 2, bovine papilloma virus, papovavirus, cytomegalovirus derived promoters or mammalian cell derived promoters, e.g. of the actin, collagen, myosin, or β-globin gene. The eukaryotic promoters may be combined with enhancing sequences such as the yeast, preferably *S. cerevisiae*, upstream activating sequences (UAS) or viral or cellular enhancers such as the cytomegalovirus IE enhancers, SV40 enhancer, immunoglobulin gene enhancer or others.

Enhancers are transcription-stimulating DNA sequences, e.g. derived from viruses such as Simian virus, polyoma virus, bovine papilloma virus or Moloney sarcoma virus, or of genomic origin. An enhancer sequence may also be derived from the extrachromosomal ribosomal DNA of *Physarum polycephalum* (PCT/EP 8500278). Suitable enhancers are also, for example, upstream activation sites derived from the yeast acid phosphatase PH05 gene.

Signal sequences may be, for example, a presequence or secretory leader directing the secretion of the polypeptide, or the like. A signal sequence is, for example, a signal or leader peptide of Aspergillus-aspartic proteinase, for example, the signal sequence shown in SEQ ID NO. 1. Further signal sequences are known from literature, e.g. those compiled in von Heijne, G., Nucleic Acids Res. 14, 4683 (1986).

Sequences necessary for the initiation and termination of transcription and for stabilizing the mRNA are commonly available from the noncoding 5'-regions and 3'-regions, respectively, of viral or eukaryotic cDNAs, e.g. from the expression hosL In an embodiment of the invention is an expression vector comprising an intron-less coding region composed of the three exons of the coding region shown in SEQ ID NO. 1 for expression of Aspergillus-aspartic proteinase in procaryotes, e.g. in *E. coli*, or preferably in yeast, more preferably in *S. cerevisiae* under the control of the GAL10 promoter, for example as in plasmid, pGALPEPE.

The invention preferably concerns an expression vector suitable for the expression of a DNA sequence encoding an Aspergillus-aspartic proteinase in an Aspergillus strain.

One type of expression vector according to the invention comprises a DNA sequence encoding an Aspergillus-aspartic proteinase, preferably of *A. niger*, under the control of a promoter which is naturally linked with the said DNA sequence, i.e. its homologous promoter. More preferred is an expression vector comprising a DNA sequence encoding PEPE of SEQ ID NO. 1, most preferably the DNA sequence shown in SEQ ID NO. 1, under the control of the promoter region shown in SEQ ID NO. 1.

If such an expression vector is used for the expression of Aspergillus-aspartic proteinase in a host strain of the species the Aspergillus-aspartic proteinase gene is originally derived from, the Aspergillus-aspartic proteinase is overexpressed because both the recombinant and the original Aspergillus-aspartic proteinase genes are active under the same expression conditions.

Another type of expression vector of the invention comprises a DNA sequence coding for Aspergillus-aspartic proteinase under the control of a promoter functional in Aspergillus, which is not naturally linked with the said DNA sequence. A promoters suitable for the expression of Aspergillus-aspartic proteinase in Aspergillus spec., in particular in *A. niger*, is, for example, a promoter of an Aspergillus spec. pectin lyase gene, preferably the promoter of the *A. niger* PLI (see EP-A-0 278 355), PLA, PLB, PLC, PLE or PLF (see EP-A-0 353 188) gene, a promoter of an Aspergillus spec. polygalacturonase gene, preferably the promoter of the *A. niger* PGI or PGII gene (see EP-Appl. EP-A421919), a promoter of an Aspergillus spec. pyruvate kinase gene, preferably the promoter of the *A. niger* pki gene (EP-Appl. EP-A-439997).

In a preferred embodiment of the invention, e.g. in the plasmid pPKIPEPE, the pyruvate kinase promoter of *A. niger* is functionally linked with the coding region shown in SEQ ID NO. 1, encoding Aspergillus-aspartic proteinase linked to its homologous signal sequence.

Process for the Preparation of an Aspersillus-aspartic Proteinase Gene

The invention also concerns a process for the preparation of a DNA molecule of the invention, i.e. such encoding an Aspergillus-aspartic proteinase of the invention, preferably such encoding a preferred form of an Aspergillus-aspartic proteinase of the invention, or for the preparation of a hybrid vector comprising such DNA molecule, said process comprising culturing a host transformed with a said DNA molecule or hybrid vector of the invention. In an alternative embodiment of the invention a DNA molecule of the invention can be prepared by chemical synthesis through nucleotide condensation.

The culturing of the hosts is carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any transformable hosts useful in the art may be used, e.g. bacteria, such as *E. coli*, fungi, such as *Saccharomyces cerevisiae*, *Kluyveromyces lactis*, higher eukaryotic cells such as insect cells or mammalian cells, e.g. CHO cells, or in particular filamentous fungi, such as Aspergillus, e.g. *A. nidulans*, *A. oryzae*, *A. carbonarius*, *A. awamori*, *A. japonicus*, and especially *A. niger*. Transformation of the hosts is carried out by conventional methods.

A DNA sequence encoding Aspergillus-aspartic proteinase can be obtained from the genome of an Aspergillus strain capable of expressing Aspergillus-aspartic proteinase, or can be prepared, for example, by culturing a host which is transformed with a recombinant DNA molecule comprising a DNA sequence encoding an Aspergillus-aspartic proteinase and, when required, isolating the desired DNA sequence therefrom.

In particular, such a DNA can be prepared by a method comprising a step selected from a) isolating genomic DNA from suitable Aspergillus cells, and selecting the desired DNA, e.g. using a DNA probe or using a suitable expression system and screening for expression of the desired polypeptide, b) isolating mRNA from suitable Aspertillus cells, selecting the desired mRNA, e.g. by hybridization with a DNA probe or by expression in a suitable expression system and screening for expression of the desired polypeptide, preparing single-stranded cDNA complementary to that mRNA, then double-stranded cDNA therefrom, c) isolating cDNA from a cDNA library and selecting the desired cDNA, e.g. using a DNA probe or using a suitable expression system and screening for expression of the desired polypeptide, d) synthesizing double stranded DNA in vitro by PCR technology of total Aspergillus DNA using oligonucleotide primers designed from the gene encoding *A. niger* pepE, or e) incorporating a double-stranded DNA obtainable according to step a), b), c) or d) into an appropriate vector, transforming a suitable host, multiplicating the host and isolating the DNA Genomic DNA may be isolated and screened for the desired DNA (step a). Genomic DNA is isolated from an Aspergillus strain capable of expressing an Aspergillus-aspartic proteinase. A genomic DNA library is prepared therefrom by digestion with suitable restriction endonucleases and incorporation into suitable vectors following established procedures. The genomic DNA library is screened with a DNA probe as described hereinafter, or expressed in a suitable expression system and the obtained polypeptides screened in conventional manner.

A genomic library can be prepared e.g. by partial digestion of genomic DNA of an A. niger strain, e.g. NW756 or N400, with e.g. Sau3AI or MboI, and cloning the high molecular weight DNA fragments in a suitable host vector, e.g. the E. coli plasmid pUN121 or a iam bda vector, e.g. EMBL4.

Other fungal strains producing a desired Aspergillus-aspartic proteinase, for example, A. japonicus, A. oryzae, A. nidulans, A. niger, may serve as source for the genomic library and other suitable vectors, e.g. those mentioned hereinbefore, may be used as recipient for the fragments.

In order to successfully screen the genomic library for DNA sequences coding for Aspergillus-aspartic proteinase a hybridizing DNA probe is necessary. This can be a synthetic DNA probe if the amino acid sequence or part thereof of a desired Aspergillus-aspartic proteinase is known, or another aspartic proteinase gene, e.g. from Neurospora crassa, or a part thereof, which hybridizes to an Aspergillus-aspartic proteinase gene.

Polyadenylated messenger RNA (step b) is isolated from the suitable cells, by known methods. Isolation methods involve, for example, homogenizing in the presence of a detergent and a ribonuclease inhibitor, e.g. heparin, guanidinium isothiocyanate or mercaptoethanol, extracting the mRNA with suitable chloroform-phenol mixtures, optionally in the presence of salt and buffer solutions, detergents and/or cation chelating agents, and precipitating mRNA from the remaining aqueous, saltcontaining phase with ethanol, isopropanol or the like. The isolated mRNA may be further purified by centrifuging in a cesium chloride gradient followed by ethanol precipitation and/or by chromatographic methods, e.g. affinity chromatography, for example chromatography on oligo(dT) cellulose or on oligo(U) sepharose. Preferably, such purified total mRNA is fractionated according to size by gradient centrifugation, e.g. in a linear sucrose gradient, or chromatography on suitable size fractionation columns, e.g. on agarose gels.

The desired mRNA is selected by screening the mRNA directly with a DNA probe, or by translation in suitable cells or cell-free systems and screening the obtained polypeptides.

The selection of the desired mRNA is preferably achieved using a DNA hybridization probe as described hereinafter, thereby avoiding the additional step of translation. Suitable DNA probes are DNAs of known nucleodde sequence, for example synthetic DNAs, cDNAs derived from mRNA coding for the desired polypeptides, or genomic DNA fragments comprising e.g. adjacent DNA sequences which are isolated from a natural source or from a genetically engineered microorganism.

Fractionated mRNA may be translated in cells, e.g. frog oocytes, or in cell-free systems, e.g. in reticulocyte lysates or wheat germ extracts. The obtained polypeptides are screened for enzymatic activity or for reaction with antibodies raised against the native polypeptide, e.g. in an immunoassay, for example radioimmunoassay, enzyme immnoassay or immunoassay with fluorescent markers. Such immunoassays and the preparation of polyclonal and monoclonal antibodies are well known in the art and are applied accordingly.

The preparation of a single-stranded complementary DNA (cDNA) from the selected mRNA template is well known in the art, as is the preparation of a double-stranded DNA from a single-stranded DNA. The mRNA template is incubated with a mixture of deoxynucleoside triphosphates, optionally radioactively labelled deoxynucleoside triphosphates (in order to be able to screen the result of the reaction), a primer sequence such as an oligo-dT residue hybridizing with the poly(A) tail of the mRNA and a suitable enzyme such as a reverse transcriptase e.g. from avian myeloblastosis virus (AMV). After degradation of the template mRNA e.g. by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of E. coli DNA polymerase I or T4 DNA polymerase. Usually, a hairpin loop stucture formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a cDNA library and screened for the desired cDNA (step c). The cDNA library is constructed by isolating mRNA from suitable cells, and preparing single-stranded and double-stranded cDNA therefrom as described above. This cDNA is digested with suitable resctriction endonucleases and incorporated into λphage, e.g. λcharon 4A or λgt11 following established procedures. The cDNA library replicated on suitable membranes, e.g. nitrocellulose membranes, charged nylon membranes, such as Hybond®, Immobilon®, or GeneScreen®, is screened by using a DNA probe as described hereinbefore, or expressed in a suitable expression system and the obtained polypeptides screened for reaction with an antibody specific for the desired compounds.

Another method for the preparation of double stranded DNA is PCR technology (step d). This method can in particular be used for the preparation of a large amount of double stranded DNA starting from a small amount of DNA or RNA with at least partly known sequences. However, also a DNA insert with unknown sequence which is flanked by known vector sequences can be used as starting material. In PCR technology DNA molecules, e.g. oligonucleotides, are used as primer for the enzymatic template-dependent synthesis of DNA. Large amounts can be prepared because the denaturing of double stranded DNA, hybridisation with the primers, and enzymatic synthesis can be sequentially repeated. The number of synthesized DNA molecules increases exponentially because it doubles each round. PCR technology is state of the art and can be conventionally applied in the present invention. The oligonucleotide primer can be designed to hybridize to DNA that would encode conserved aspartic protease protein sequences based on comparisons between known aspartic proteases. PCR technology is well known in the art and conventional PCR techniques may be applied to the present invention, e.g. those described in: M.A. Innis et al. (eds.), PCR protocols. A guide to methods and applications. Academic Press, San Diego (1990).

A variety of methods are known in the art for the incorporation of double-stranded cDNA or genomic DNA into an appropriate vector (step e). For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possiblities are the addition of synthetic linkers to the termini of the double-stranded DNA, or the incorporation of the double-stranded DNA into the vector by blunt- or staggered-end ligation. Appropriate vectors will be discussed in detail hereinbelow.

Transformation procedures for transforming appropriate host cells with the obtained hybrid vector and the selection and multiplication of transformed host cells are well known in the art. Examples for such methods are given further below.

The isolation of the desired DNA, mutants and fragments therof according to the invention is achieved by methods known in the art, e.g. extraction with phenol and/or chloroform. Optionally, the DNA can be further manipulated e.g. by treatment with mutagenic agents to obtain mutants, or by digestion with restriction enzymes to obtain fragments, modify one or both termini to facilitate incorporation into the vector, remove intervening sequences and the like.

The nucleotide sequence of a DNA according to the invention can be determined by methods known per se, for example by the Maxam-Gilbert method using end-labelled DNA or by the dideoxy chain termination method of Sanger.

Aspergillus-aspartic proteinase gene sequences of the present invention can also be prepared by an in vitro synthesis according to conventional methods. The in vitro synthesis is especially applicable for the preparation of smaller fragments of an Aspergillus-aspartic proteinase gene coding for fragments of Aspergillus-aspartic proteinase with aspartic protease activity. In vitro synthesis is also particularly applicable for the synthesis of DNA coding for a promoter or a signal peptide. The in vitro synthesis is preferably applied to the Aspergillus-aspartic proteinase gene derived from *A. niger* or fragments thereof, most preferably to the pepE gene shown in SEQ ID NO. 1 or the promoter or signal sequence thereof.

In performing the present invention, an aspartic proteinase gene of another species, e.g. *N. crassa*, or a fragment thereof can be used as probe for identifying an Aspergillus spec., e.g. an *A. niger*, aspartic proteinase mRNA in an RNA fraction or a aspartic proteinase DNA in a genomic or cDNA library. From the primary sequence of the *A. niger* gene and comparison to other proteases the coding region of the protease can be deduced and the relationship of the gene to the aspartic proteinase gene family can be confirmed. The gene obtained can be used for the preparation of recombinant protease as outlined in detail hereinbelow.

Synthetic DNA probes can be ordered or synthesized according to known methods. Mixtures of the desired oligonucleotides can be obtained by using mixtures of two, three or four nucleotides dA, dC, dG and/or dT in protected form or the corresponding dinucleotide coupling units in the appropriate condensation step as described by Y. Ike et al. (Nucleic Acids Research 11, 477, 1983).

For hybridization, the DNA probes are labelled, e.g. radioactively labelled by kinase reaction. The hybridization of the size-fractionated mRNA with the DNA probes containing a label is performed according to known procedures, i.e. in buffer and salt solutions containing adjuncts, e.g. calcium chelators, viscosity regulating compounds, proteins, non-homologous DNA and the like, at temperatures favoring selective hybridization, e.g. between 0° C. and 80° C., for example between 25° C. and 50° C. or around 65° C., preferably at around 20° lower than the hybrid double-stranded DNA melting temperature.

Transformed Hosts and Preparation Thereof

Furthermore, the invention concerns host cells transformed with a hybrid or expression vector of the invention, preferably such encoding the preferred forms of the Aspergillus-aspartic proteinase of the invention.

Examples of suitable hosts, particularly for multiplication of the recombinant DNA molecules of the invention, are microorganisms which are devoid of or poor in restriction enzymes or modification enzymes, such as bacteria, in particular strains of *Escherichia coli*, for example *E. coli* X1776, *E. coli* Y1090, *E. coli* W3110, *E. coli* HB101/ LM1035, *E. coli* JA 221, *E. coli* DH5α, or preferentially *E. coli* DH5αF', JM109, MH1 or HB101, or *E. coli* K12 strain. Suitable hosts are also other procaryotic cells, e.g. *Bacillus subtilis*, *Bacillus stearothermophilus*, Pseudomonas, Haemophilus, Streptococcus and others, and yeasts, for example *Saccharomyces cerevisiae* such as *S. cerevisiae* GRF 18. Further suitable host cells are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells.

Examples of suitable cells for the expression of an Aspergillus-aspartic proteinase gene of the invention are the cells mentioned hereinbefore transformed with an appropriate expression vector and additionally suitable insect cells transformed with an appropriate Baculovirus expression vector, and, in particular, filamentous fungi, for example Penicillium, Cephalosporium or preferentially Aspergillus spec., e.g. *A. carbonarius*, *A. awamori*, *A. nidulans*, *A. oryzae* or more preferentially *A. niger*, transformed with an appropriate expression vector.

The invention concerns also a method for the preparation of such transformants comprising treatment of a suitable host cell under transforming conditions with a DNA molecule or hybrid vector of the invention, optionally together with a selectable marker gene and optionally selecting the transformants. The Aspergillus-aspartic proteinase gene may also become integrated into the host genome after transfornation, in particular if eukaryotic cells, for example Aspergillus spec. is used as host.

Transformation of microorganisms is carried out according to conventional methods as described in the literature, for example for *S. cerevisiae* (A. Hinnen et al., Proc. Natl. Acad. Sci. U.S.A., 75, 1929,1978), for *B. subtilis* (Anagnostopoulos et al., J. Bacteriol. 81, 741, 1961), for *E. coli* (M. Mandel et al., J. Mol. Biol. 53, 159, 1970), and for Aspergillus [F. Buxton et al., Gene 37:207–14(1985), D. J. Balance et al., Biochem. Biophys. Res. Commun. 112:284–9 (1983)]

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the hybrid vector.

The transformation of fungi such as yeast or Aspergillus spec. comprises, for example, steps of enzymatic removal of the cell wall by means of glucosidases, treatment of the obtained spheroplasts with the hybrid vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably chosen so as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient in said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibres, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum titer of the polypeptide or derivative of the invention is obtained. Thus, an E. coli or yeast strain is preferably cultured under aerobic conditions by submerged culture with shaking or stirring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

In order to allow selection of the transformed from the nontransformed cells, the DNA molecules of the invention carry a selection marker or, alternatively, the cells are cotransformed with a second vector containing such marker. As in other systems such selection marker is an expressible, structural gene, the expressed polypeptide of which (an enzyme) provides resistance against compounds toxic to the receipt organism or which completes the enzyme system of a mutant lacking such essential polypeptide. Such marker genes suitable for selection of transformed filamentous fungal cells are, for example, the known qa-2, pyrG, pyr4, trpC, amdS or argB genes.

As described in EP-A-0 278 355 a marker gene, named pyrA, was isolated from the genomic library of A. niger, which is related to and has similar function as pyrG of A. nidulans and pyr4 of N. crassa, namely producing the enzyme orotidine 5'-phosphate decarboxylase. This enzyme catalyses the decarboxylation of orotidine 5'-phosphate to uridylic acid (uridine 5'-phosphate) and also of fluoro-orotic acid to the toxic fluoro-uridine. However, DNA of any other pyr gene coding for orotidine-5'-phosphate decarboxylase may be used. From a positive clone named E. coli BJ5183/pCG59D7 (DSM 3968), the plasmid pCG59D7, comprising the pyrA gene, was isolated and used for cotransformation of an A. niger pyrA⁻ mutant. Such pyrA⁻ mutant is defective in the orotidine 5'-phosphate decarboxylase gene and therefore is unable to produce the corresponding enzyme. Such mutant was prepared by treating conidiospores of A. niger N756 under mutating UV-irradiation and colonies surviving in the presence of fluoro-orotic acid and uridine are selected. Colonies surviving in the presence of fluoroorotic acid and absence of uridine are eliminated. The remaining uridine-requiring mutants, according to their ability of being transformable, belong to two complementation groups pyrA and pyrB, represented by A. niger mutants An8 and An10, respectively. They are treated in the form of protoplasts thereof under transforming condition with the pyrA containing plasmid pCG59D7 (DSM 3968). Only the A. niger An8 (DSM 3917) colonies were found to be transformed and to contain the pyrA gene as evidenced by the hybridizing ability of digested DNA thereof with DNA of pUN 121.

Process for the Preparation of Aspergillus-aspartic Proteinase

The invention also concerns a process for the preparation of an Aspergillus-aspartic proteinase of the invention, preferably the preferred forms thereof, comprising culturing a host transformed with an expression vector of the invention under conditions suitable for the expression of the Aspergillus-aspartic proteinase gene. When required, the polypeptide is isolated in conventional manner. Depending on the construction of the expression vector, Aspergillus-aspartic proteinase is either produced or, if a signal sequence is present, produced and secreted out of the cytoplasm into the media or other cellular compartments.

Whether a selected host is suitable for the expression or not depends mainly on the regulatory sequences chosen for constructing the expression vector, in particular on the promoter.

For example, if a promoter derived from an Aspergillus, preferably A. niger, gene is used for the expression of an Aspergillus-aspartic proteinase gene of the invention, an Aspergillus strain, preferably A. niger, is a suitable host. However, if a promoter not derived from an Aspergillus gene is used for the construction of an expression vector of the invention, other hosts are suitable for the expression, e.g.

bacteria such as *E. coli,* or yeast, such as *S. cerevisiae.* Suitable hosts and promoters for the preparation of polypeptides according to the invention are also those suitable for transformation given hereinbefore.

In particular, the invention concerns a process in which a transformed Aspergillus host is expressing the exogenous Aspergillus-aspartic proteinase gene under conditions in which endogenous Aspergillus-aspartic proteinase genes are active and thus expressing more than the natural amount of Aspergillus-aspartic proteinase due to the increased gene dose. For this purpose, the Aspergillus host, in particular *A. niger,* is transformed with an expression vector comprising an Aspergillus-aspartic proteinase gene under the control of its homologous, i.e. naturally linked, expression control sequences, in particular promoter and signal sequence.

In particular, the invention also concerns a process in which a transformed Aspergillus host is expressing the exogenous Aspergillus-aspartic proteinase gene to a higher level or under different conditions than the endogenous gene because it is fused to a different promoter.

The conditions for maximal expression of the exogenous gene or genes depend on the selected expression system. For example, if a promoter of a pectin lyase (PL) or of a polygalacturonase (PG) gene of *A. niger* is used, the expression of the Aspergillus-aspartic proteinase gene linked therewith is inducible in an *A. niger* cell by addition of pectin or pectin degradation products to the culture medium. In the presence of sufficient glucose, however, the promoter is not inducable, if an *A. niger* strain, e.g. An8 (DSM 3917), is used as host. This means, an Aspergillus-aspartic proteinase gene under the control of an *A. niger* PL or PG promoter is "catabolite repressed" in *A. niger.* However, if another Aspergillus strain is used, preferentially *A. oryzae* or most preferentially *A. nidulans,* an Aspergillus-aspartic proteinase gene under the control of an *A. niger* PL or PG promoter is expressed constitutively, i.e. also in the absence of pectin and/or in the presence of glucose. It can therefore be advantageous to express an Aspergillus-aspartic proteinase gene under the control of an *A. niger* PL or PG promoter in an Asperollus host other than *A. niger,* preferentially *A. oryzae* or most preferentially *A. nidulans,* because, for example, glucose instead of pectin can be added to the nutrient medium as energy and carbon source during the expression of the gene.

If an Aspergillus, preferably *A. niger,* pyruvate kinase promoter is used for the expression of an Aspergillus-aspartic proteinase gene, the gene is expressed if a minimal medium with glucose as carbon- and energy source is used.

It is now possible to overexpress Aspergillus-aspartic proteinase, whereby various methods can be applied. A purified single Aspergillus-aspartic proteinase can be prepared by a method in which a suitable host which is not capable of expressing any Aspergillus-aspartic proteinase or which expresses Aspergillus-aspartic proteinase in low amount or which does not express Aspergillus-aspartic proteinase under the induction conditions used for the expression of the exogenous Aspergillus-aspartic proteinase gene, is transformed with a hybrid vector comprising a structural gene coding for an Aspergillus-aspartic proteinase, preferably from *A. niger,* most preferably PEPE shown in SEQ ID NO. 1, or a fragment of an Aspergillus-aspartic proteinase aspartic protease activity, and that said structural gene is expressed. If a host not capable of expressing any other aspartic proteinase is used, the respective single Aspergillus-aspartic proteinase can be obtained in pure form, that means uncontaminated by any other Aspergillus-aspartic proteinase.

A host not capable of expressing any Aspergillus-aspartic proteinase is either a microorganism having no corresponding gene or an Aspergillus strain whose expression of endogeneous Aspergillus-aspartic proteinase genes are suppressed in an appropriately conditioned growth medium, whereas the exogenous Aspergillus-aspartic proteinase promoter operatively linked with the desired Aspergillus-aspartic proteinase structural gene, e.g. an *A. niger* derived promoter, is active under these conditions or where the Aspergillus-aspartic proteinase gene is fused to another promoter.

Other promoters and strains suitable for the preparation of Aspergillus-aspartic proteinase are the given hereinbefore in the description of the expression vectors of the invention.

Aspergillus-aspartic Proteinase and Use Thereof

The invention also concerns a pure Aspergillus aspartic protease per se, herein named "Aspergillus-aspartic proteinase". Such a protease is understood as (a) being derived from Aspergillus spec., (b) exhibiting protease activity due to a catalytic aspartic acid residue at the active site and (c) having sufficient amino acid sequence homology with known aspartic proteases for being grouped into the aspartic proteinase family. Included within the term Aspergillus-aspartic proteinase are also fragments of such an enzyme which retain aspartic protease activity.

The invention concerns preferentially a pure Aspergillus-aspartic proteinase of *Aspergillus niger,* preferably the aspartic protease PEPE having the amino acid sequence shown in the sequence listing under SEQ ID. NO. 1, and fragments and mutants thereof which retain aspartic protease activity.

The invention concerns further enzymatic compositions comprising one or more of an Aspergillus-aspartic proteinase and/or a derivative thereof with aspartic protease activity and/or biologically acceptable salts thereof optionally in a predetermined combination with one or more suitable enzymes having other than Aspergillus-aspartic proteinase activity.

Aspergillus Strain Deficient in Aspergillus-aspartic Proteinase

The invention also concerns a mutated Aspergillus strain, preferably a mutated *A. niger* strain, deficient in an endogenous Aspergillus-aspartic proteinase gene. Preferred is an *A. niger* strain deficient in the pepE gene shown in SEQ ID NO. 1. Preferred is also an *A. niger* strain deficient the pepE gene and deficient in other protease genes such as pepA, pepB, pepC or pepD.

A mutated Aspergillus strain of the invention having a defective Aspergillus-aspartic proteinase gene can in a preferred embodiment of the invention be prepared by gene disruption, i.e. a DNA sequence corresponding to the endogenous Aspergillus gene which is desired to be destroyed is in vitro mutated to a defective gene and transformed into the Aspergillus host cell. Due to a homologous recombination event in the cell the intact endogenous gene is replaced by the defective exogenous one. Usually the exogenous gene is destroyed by inserting a marker gene into the coding region. This leads to a defective gene which can be easily monitored and used for selecting transformants with the corresponding endogenous gene disrupted. However, also other methods for mutagenesis may be used for the preparation of a mutated Aspergillus strain, preferably a mutated *A. niger* strain, in which an endogenous Aspergillus-aspartic proteinase gene is mutated in such way that no functional Aspergillus-aspartic proteinase can be expressed.

In a most preferred embodiment of the invention an *A. niger* strain is transformed with a hybrid vector comprising a defective mutant of the pepE gene shown in SEQ ID NO.

1, e.g. a disrupted pepE gene having a selection marker gene inserted, e.g. as comprised in plasmid pPEPEPYRA described in the accompanying examples, and transformants are selected.

A mutated Aspergillus strain of the invention having a defective Aspergillus-aspartic proteinase gene is useful for the expression of an improved production of heterologous or homologous proteins either intra- or extracellularly The expression of heterologous or homologous proteins in Aspergillus spec. can be achieved according to conventional methods. Usually, an expression vector is constructed comprising a homologous or heterologous gene operably linked with a homologous or heterologous promoter functional in Aspergillus and optionally with other expression control sequences functional in Aspergillus, e.g. those defined hereinbefore. When required, the polypeptide is isolated in a conventional manner. Depending on the construction of the expression vector the products are either produced in the host cell or, if a signal sequence is present, are produced in the cell and secreted.

Structural genes in this context are, for example, structural genes which originate from viruses, procaryotic cells or eucaryotic cells and which may be derived from genomic DNA or from cDNA prepared via the mRNA route or may be synthesized chemically, coding for a wide variety of useful polypeptides, including glycosylated polypeptides, in particular of higher eukaryotic, especially mammalian, such as animal or especially human origin, such as enzymes which can be used, for example, for the production of nutrients and for performing enzymatic reactions in chemistry, or polypeptides, which are useful and valuable for the treatment of human and animal diseases or for the prevention thereof, for example, hormones, polypeptides with immunomodulatory, anti-viral and anti-tumor properties, antibodies, viral antigens, vaccines, clotting factors, foodstuffs and the like.

Examples of such structural genes are e.g. those coding for Aspergillus polygalacturonase, e.g. PGI or PGII, or Aspergillus pectin lyase, e.g. PLI, PLA, PLB, PLC, PLE and PLF, or hormones such as secretin, thymosin, relaxin, calcitonin, luteinizing hormone, parathyroid hormone, adrenocorticotropin, melanoycte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFβ, growth hormones, such as human or bovine growth hormones, interleulin, such as interleukin-1 or -2, human macrophage migration inhibitory factor (MIF), interferons, such as human α-interferon, for example interferon-αA, αB, αD or αF,β-interferon, γ-interferon or a hybrid interferon, for example an αA-αD- or an αB-αD-hybrid interferon, especially the hybrid interferon BDBB, proteinase inhibitors such as $α_1$-antitrypsin, SLPI and the linke, hepatitis virus antigens, such as hepatitis B virus surface or core antigen or hepatitis A virus antigen, or hepatitis nonA-nonB antigen, plasminogen activators, such as tissue plasminogen activator or urokinase, tumour necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, calcitonin, human calcitonin-related peptide, blood clotting factors, such as factor IX or VIIIc, erythropoietin, eglin, such as eglin C, hirudin, desulfatohirudin, such as desulfatohirudin variant HV1, HV2 or PA, human superoxide dismutase, viral thymidin kinase, β-lactamase, glucose isomerase. Preferred genes are those coding for a human α-interferon or hybrid interferon, particularly hybrid interferon BDBB, human tissue plasminogen activator (t-PA), hepatitis B virus surface antigen (HBVsAg), insulin-like growth factor I and II, eglin C and desulfatohirudin, e.g. variant HV1.

The most preferred embodiments are those described in the accompanying examples.

EXAMPLES

The following examples serve to illustrate the invention, however, are in no way intended to restrict it.

The abbreviations have the following meanings:

| | |
|---|---|
| BSA | bovine serum albumin |
| DTT | 1,4-dithiothreitol |
| EDTA | ethylenediamine tetra acetic acid, disodium salt |
| IPTG | isopropyl-β-D-thiogalactopyranoside |
| kbp | kilo base pairs |
| PEG | polyethylene glycol |
| SDS | sodium dodecyl sulfate |
| Tris | tris (hydroxymethyl) aminomethane |
| X-gal | 5-bromo-4-chloro-3 indolyl-β-galactoside |
| Buffers, media, reagents | |
| SM | 100 mM NaCl, 8.1 mM $MgSO_4$, 50 mM Tris-HCl pH 7.5, 0.01 % gelatin |
| LB | 1% trypticase peptone (BBL), 0.5% yeast extract (BBL), 1% NaCl and 0.5 mM Tris-HCl pH 7.5 |
| LM | 1% trypticase peptone (BBL), 0.5% yeast extract (BBL), 10 mM NaCl and 10 mM $MgCl_2$ |
| SSC | 0.15 M NaCl, 0.015 M tri-sodium citrate |
| PSB | 10 mM Tris-HCl, pH 7.6, 100 mM NaCl, 10 mM $MgCl_2$, |
| TE | 10 mM Tris-HCl pH 8.0, 0.1 mM EDTA pH 8.0 |
| minimal medium | 1 liter contains 1.5 g $KH_2PO_4$, 0.5 g KCl, 0.5 g $MgSO_4.7\ H_2O$, 0.9 mg $ZnSO_4.7\ H_2O$, 0.2 g $MnCl_2.4\ H_2O$, 0.06 mg $CoCl_2.6\ H_2O$, 0.06 mg $CuSO_4.5\ H_2O$, 0.29 mg $CaCl_2.62\ H_2O$, 0.2 mg $FeSO_4.7\ H_2O$, nitrogen and carbon sources as specified in the text or 6 g $NaNO_3$ and 10 g glucose per liter if these sources are not explicitly mentioned, adjusted to pH 6.0 with NaOH |
| complete medium | minimal medium with 6 g $NaNO_3$ and 10 g glucose per liter, plus per liter 2 g trypicase peptone (BBL), 1 g casaminoacids (Difco), |

| | -continued |
|---|---|
| | 1 g yeast extract (BBL), 0.5 g ribonucleic acid sodium salt from yeast (ICN, Cleveland, U. S. A.), 2 ml vitamin solution, adjusted to pH 6.0 with NaOH |
| vitamin solution | per 100 ml 10 mg thiamine, 100 mg riboflavin, 10 mg panthotenic acid, 2 mg biotin, 10 mg p-aminobenzoic acid, 100 mg nicotinamide, 50 mg pyridoxin-HCl |
| TBE | 1 liter contains 4 ml of a 0.5 M EDTA pH 8.0 solution, 10.8 g Tris and 5.5 g $H_3BO_3$ |
| phenol | phenol treated as described by Maniatis et al., Molecular Cloning; A Laboratory Manual, Cold Spring Harbour Laboratory 1982 (p438) |
| sample buffer | 10% (v/v) glycerol, 100 mM EDTA pH 8.0 and 0.01% bromophenol blue |
| RNase A | RNase A treated as described by Maniatis et al., Molecular Cloning; A Laboratory Manual, Cold Spring Harbour Laboratory 1982 (p451) |
| The following strains and vectors are used: | |
| A. niger N400 | wild type. |
| A. niger An8 | uridine auxotrophic mutant of the pectinase complex highly producing strain A. niger N756, disclosed in EP-A-0 278 355, deposited as DSM 3917. |
| E. coli LE392 | F⁻, hsdR514 (rk⁻, mk⁺), supE44, supF58, LacY1, or (lac1ZY)6, galK2, galT12, metB1, trpR55, λ⁻. |
| E. coli DH5αF | F', endA1, hsdR17, (rk⁻, mk⁺), supE44, thi-1, recA1, gryA, relA1,)80Ølac Z M15, Δ(lac ZYA-argF)U169, λ⁻. |
| EMBL4 | EMBL4 is a lambda replacement vector with a cloning capacity of 9–23 kbp (Frischauf et al., J. Mol Biol. 170:827–842, 1983). It contains a multiple cloning region between the lambda arms and the nonessential stuffer region. This allows multiple restriction enzyme digestions to be performed in a manner such that religation of the stuffer to the vector arms is reduced as the foreign DNA of interest is inserted. The vector also makes use of the Spi phenotype to provide a direct selection for recombinants (Zissler et al. in: A.D. Hershey (ed.) The Bacteriophage lambda, Cold Spring Harbour Laboratory, 1971). |

In the Examples a series of oligonucleotides are used in PCR technology. The following is a short characterization of the oligos. The sequences are shown in the sequence listing.

oligonucleotide 1: Designed to prime just before the BamHI site in the pki promoter.

oligonucleotide 2: Designed to insert a PstI site just before the ATG of pyruvate kinase.

oligonucleotide 3: Designed to insert a PstI site just before the ATG of pepE.

oligonucleotide 4: Designed to insert a XhoI site just after the stop codon of pepE.

oligonucleotide 5: Designed to insert a SalI site just after the stop codon of pyruvate kinase.

oligonucleotide 6: Designed to put a BamHI site at the end of the pyruvate kinase terminator.

oligonucleotide 7: Designed to loop out the first intron in pepE.

oligonucleotide 8: Designed to loop out the second intron in pepE.

oligonucleotide 9: Designed to loop out the third intron in pepE.

oligonucleotide A: Designed to prime runoff transcript from pepE RNA.

oligonucleotide B: Designed as PCR primer to amplify parts of the first and third and all of the second exons of pepE.

oligonucleotide C: Designed to prime cDNA synthesis from pepE RNA and to amplify parts of the first and the third and all of the second exons of pepE.

oligonucleotide D: Designed as PCR primer to amplify parts of the third and fourth exons of pepE.

oligonucleotide E: Designed to prime cDNA synthesis from pepE RNA and to amplify parts of the third and fourth exons of pepE.

Example 1

Construction of a Genomic Library of *Aspergillus niger*

Example 1.1: Isolation of High Molecular Weight DNA from *A. niger* N400

Conidiospores of *Aspergillus niger* strain N400 are inoculated in 200 ml minimal medium to a final spore density of $10^6$ spores/ml and shaken in 1l Erlenmeyers for 24 h at 28° C. at 300 rpm. The mycelium is harvested by filtration through Myracloth on a Buchner funnel, washed with cold sterile saline, frozen in liquid nitrogen and either stored at −60° C. or used directly. The method used for isolation of DNA to prepare the genomic library is based on the procedure described by Yelton et al. [Proc. Natl. Acad. Sci. U.S.A. 81:1470–1474(1984)].

For library construction, 10 g mycelium is ground in liquid nitrogen in 1 g portions in a Braun microdismembrator. The ground mycelium is transferred to a 1l sterile erlenmeyer, containing 200 ml extraction buffer (50 mM EDTA pH 8.5, 0.2% SDS) and 200 μl diethylpyrocarbonate. The mixture is slowly warmed up to room temperature and then heated for 20 min to 68° C. with occasional shaking. The suspension is cooled to room temperature and centrifuged for 15 min at 12,000×g. 1/16 volume of an 8M potassium acetate solution pH 4.2 is added to the supernatant and the mixture is left on ice for 1 h. The precipitate is removed by centrifugation (20 min.; 16,000×g; 4° C.). The nucleic acids are precipitated from the supernatant by an incubation with 0.6 volume of isopropanol on ice for 15 min. The precipitated nucleic acid is collected by centrifugation (10 min.; 6,000×g; 4° C.), washed with 70% ethanol and briefly dried. The pellet is suspended in 10 ml TE containing 20 μg/ml RNAse A, (Boehringer, Mannheim) and incubated for 15 min at 37° C. The DNA is treated with nuclease free pronase (1 mg/ml final concentration) (Kochlight, Coinbrook) for 1 h at 37° C.

8.5 g CsCl is dissolved in 9 ml of the DNA solution obtained, 0.2 ml 10 mg/ml ethidium bromide is added and this solution is either centrifuged in a Beckman SW41 rotor for 60 h at 33,000 rpm, or in a Beckman 50 Ti rotor for 40 h at 45,000 rpm. The DNA band is collected and the ethidium bromide is removed by multiple extraction with isopropanol equilibrated with a satured solution of NaCl in water. 5 volumes of TE are added and the DNA solution is sequentially treated with TE saturated phenol, phenol/chloroform/isoamylalcohol 25:24:1 and chloroform/isoamylalcohol 24:1. The DNA is precipitated by addition of 0.1 volume of 3M sodium acetate pH 5.2, 2.5 volumes of ethanol and an overnight incubation at −20° C. The precipitate is collected by centrifugation (1 h, 30,000×g; 4° C.), washed with 70% ethanol, dried and dissolved in 400 µl TE.

Example 1.2: Partial Digestion of *A. niger* N400 DNA with MboI and Isolation of Fragments To test for the MboI concentration which gives the largest amount of DNA fragments between 13.6 and 23 kbp, 1 µg portions of *A. niger* N400 DNA are digested in the appropriate buffer recommended by the supplier with decreasing amounts of MboI (0.5–0.001 U) for 1 h at 37° C. in a volume of 10 µl. The reaction is stopped by the addition of 1 µl 0.25M EDTA, and the samples are loaded on a 0.6% agarose gel in TBE buffer, containing 1 µg/ml ethidium bromide. The MboI concentration required to give a high yield of the desired 13.6–23 kbp fragments is about 0.02 U/µg DNA. Accordingly, 200 µg of DNA in a total volume of 2 ml are digested. After 1 hr at 37° C. EDTA is added to a final concentration of 25 mM, the enzyme is heat-inactivated at 65° C. for 10 min and the DNA is precipitated, washed, dried and dissolved in 400 µl TE. The fragmented DNA is separated on a 0.4% preparative agarose gel at 4° C. and 40 V (3 V/cm). Fragments of the correct size are cut out of the gel and the DNA is electroeluted from the gel in a sterile dialysis tube in 2 ml TBE for 2–3 h at 100 V. The current is reversed for 30s, and the buffer containing the DNA is collected. The fragments are then concentrated by ethanol precipitation and dissolved in 100 µl TE.

Example 1.3: Preparation of Vector DNA

The genomic library of *A. niger* strain N400 is constructed in the lambda vector EMBL4. The vector, which has a cloning capacity of 9–23 kbp, is described by Frischauf et al. [J. Mol. Biol. 170:827–842(1983)] and Karn et al. [Proc. Natl. Acad. Sci. U.S.A. 77:5172–76(1980)] and can be purchased from Promega Biotechnology Inc. To avoid two inserts originating from different parts of the genome being cloned into one phage, a minimal fragment length of 13.6 kbp is used for cloning.

10 µg lambda EMBL4 DNA is digested to completion with 50 units of BamHI in the buffer recommended by the supplier in a volume of 100 µl for 2 h at 37° C. The enzyme is inactivated for 10 min at 65° C. The NaCl concentration is raised to 150 mM and 50 units of SalI are added and incubation at 37° C. continues for another 2 h. After addition of EDTA to 25 mM and inactivation of the enzyme by heating for 10 min at 65° C. The solution is extracted with equal volumes of phenol (TE saturated), phenol/chloroform/isoamylalcohol 25:24:1, and chloroform/isoamylalcohol (24:1). To eliminate the small BamHI/SalI polylinker fragments, the DNA is precipitated with 0.6 volume of isopropanol after the addition of 0.1 vol. 3M sodium acetate pH 5.2. After 15 min on ice and 15 min centrifugation at 12,000×g at 4° C., the precipitate is thoroughly washed with 70% ethanol, dried and dissolved in 40 µl TE.

Example 1.4: Ligation and in Vitro Packaging of Genomic *A. niger* N400 DNA Fragments It is essential that the cos sites of the vector prepared according to example 2.3 are annealed prior to the ligation reaction. The vector in 100 mM Tris-HCl pH 7.5 and 10 mM $MgCl_2$ is heated for 10 min at 65° C. and then annealed for 1 h at 42° C. From test ligations a ratio of vector to fragments of approximately 1:1 (by weight) is found to give most recombinants. Ligation took place in 50 mM Tris HCl pH 7.5, 10 mM $MgCl_2$, 10 mM DTT and 1 mM ATP, using 9.5 µg of vector and 10 µg of DNA fragments in a total volume of 100 µl. DNA ligase (BRL) is added at a concentration of 0.5 U/µg DNA and the ligation mixture is incubated overnight at 14° C. To test for ligation a sample of the ligated DNA is run on an agarose gel. Also, as a control 0.5 µg of vector is ligated without the addition of fragments in a 5 µl volume.

The ligation mixture is concentrated by ethanol precipitation and dissolved in 20 µl TE prior to in vitro packaging. In vitro packaging is done with Promega Packagene extracts according to the instruction of the manufacturer using 10 µl portions to package 1 µg of DNA. 1 µg of the high molecular weight control phage lambda cI857 Sam7, supplied with the extracts, is separately packaged as a control. After packaging, 500 µl of phage solution buffer (PSB) and 5 µl of chloroform are added. The recombinant phage stocks can be stored at 4° C.

Example 1.5: Titration and Amplification of the *A. niger* strain N400 Genomic Library Cells of *E. coli* NM539 are grown on LB medium containing 0.2% maltose, 10 mM $MgSO_4$ and 1 mM $CaCl_2$ to an optical density (600 nm) of 1.0. 0.2 ml aliquots of this culture are added to 0.1 ml of an appropriate phage dilution in PSB. After adsorption of the phages for 20 min at 37° C., 3 ml 0.6% LB top-agar at 45° C. is added, the mixture is plated on LB agar plates and these are incubated overnight at 37° C. The number of plaque forming units (pfu) per ml phage suspension are $12 \times 10^5$ and $4.2 \times 10^5$ pfu/ml for two phage stocks prepared according to example 1.4. After subtracting the background which is calculated from the control ligations without fragments (17% and 40% respectively) the absolute number of recombinants is $6 \times 10^5$. The DNA contained in the recombinants is equivalent to more than 200 of the *Aspergillus niger* genomes.

To amplify the library, 80 µl aliquots of both phage stocks are used to infect *E. coli* NM539 cells which are plated in LB top-agarose on LB agar plates and then incubated overnight at 37° C. The phages are eluted from the agarose by gently shaking the plates with 5 ml PSB per plate for 1 h at room temperature. The PSB is collected, centrifuged (10 min at 6000×g) to remove bacteria and chloroform is added (05% final concentration). Both phage stocks, which are amplified approximately to the same extent, are then mixed (40 µl stock), titrated ($8 \times 10^9$ pfu/ml) and stored at 4° C.

Example 2

Preparation of a *N. crassa* pep4 Probe

Example 2.1: Preparation of the *N. crassa* Probe

Plasmid pNCPEP4 contains a 3.8 kb fragment of *N. crassa* DNA, that encodes the *N. crassa* pep4 gene. Part of the coding region can be conveniently excised with SalI. The plasmid pNCPEP4 is therefore digested with SalI and the fragments are separated on a 1.2% agarose gel. The 0.6 kb fragment is cut out and the DNA is electroeluted. 100 ng of this fragment is nick translated with $^{32}$P-dATP as the labelled nucleotide and used immediately for either Southern or plaque lift probings.

Example 2.2: Southerns of *A. niger* DNA

2 μg aliquots of *A. niger* DNA, prepared as described above, are digested with either BamHI or HindIII and separated on a 0.8% agarose gel. After photographing the ethidium bromide stained gel the DNA is transfered to nitrocellulose filters by capillary blotting [Southern, E. M., J. Mol. Biol. 98:503–517(1975)] and hybridised as described in example 3 with the labelled yeast PRB probe. Separate strips of nitrocellulose containing both digests are submitted to a variety of washing regimens to determine the conditions that gave the strongest signal to noise ratio. We found that one wash in 2×SSC for thirty minutes at room temperature followed by two thirty minute washes at 56° C. in 2×SSC gives the best results.

Example 3

Screening of the *A. niger* N400 Library with the *N. crassa* pep4 Probe

Part of the genomic library of Aspergillus niger strain N400 described above (Example 1) is diluted in SM and 0.1 ml portions each containing about 2000 pfu are plated. Host cells are prepared by inoculating 50 ml of LB-medium supplemented with 0.2% maltose with 0.5 ml of an overnight culture of *E. coli* NM539 in LB-medium, shaking for 4 h at 250 rpm at 37° C., followed by the addition of 0.5 ml 1M $MgSO_4$ and of 0.5 ml 0.5 $CaCl_2$. 0.2 ml aliquots of these cells are each mixed with a 0.1 ml portion of the phage suspension and incubated at room temperature for half an hour. Then 3 ml of 0.7% agarose in LM-medium at 47° C. are added, briefly vortexed and immediately plated on LM agar plates. The plates are incubated overnight at 37° C. and chilled for 2 h at 4° C.

From each plate two replicas are made according to the Benton and Davis plaque hybridization method [Benton, W. D. and Davis, R. W., Science 196:180–182(1977)]. The first filter (Schleicher and Schuell BA85) is placed on top of the plate for 1 min, the second replica for 2 min and the position of the replicas is marked using India ink. After removing the filters they are placed in a dish containing 100 ml of a denaturing solution (1M NaCl, 0.5M NaOH) for 0.5 min, and then for 1 min in 100 ml neutralizing solution (0.5M Tris-HCl pH 7.5, 1.5M NaCl). The filters are transferred to a dish containing 3×SSC, are gently rubbed with a gloved hand to remove bacterial debris and are rinsed with 3×SSC. The filters are blotted, dried for 10 min at room temperature and baked on Whatman 3 MM paper in an oven at 80° C. for 2 h.

The baked filters are wetted in 3×SSC, washed in this solution for 1 h at room temperature and then transferred to a dish containing 250 ml prewarmed (56° C.) prehybridization mixture (6×SSC, 10×Denhardt's (0.2% BSA, Boehringer fraction V; 0.2% Ficoll 400, Pharmacia; 0.2% polyvinylpyrrolidone-10, Sigma), 0.1% SDS and 0.1 mg/ml sheared and freshly denatured herring sperm DNA). After 1 hr prehybridization at 56° C. in a shaking water baththe filters are washed once for half an hour in 250 ml prewarmed (56° C.) hybridization mixture, which is the same as the prehybridization mixture except it lacks the herring sperm DNA. Then the filters are transfered to a dish containing 150 ml of prewarmed (56° C.) hybridization mixture to which the previously labeled probe is freshly added.

After hybridising for 14 h at 65° C. the filters are washed once in 250 ml, followed by washing at room temperature and then at 56° C. in 250 ml 2×SSC, each for 30 min. The filters are dried and exposed to Kodak XAR5 film for one to three days at −70° C., using an intersifying screen.

In this way, 3 positive signals are obtained from the 3 plates screened. Positive plaques are punched out with a sterile Pasteur pipette by carefully positioning the plates on the autoradiogram using the ink markers. The pieces of agar containing the positive plaques are added to 1 ml of SM and 2.5 μl of chloroform is added. The phages are allowed to diffuse out of the agar for one hour at room temperature, occaissionally vortexing and then incubated overnight at 4° C. The agar and cell debris are removed by centrifugation for 5 min, 2.5 μl of chloroform is added and the phage stocks are stored at 4° C.

The positive clones are named λ1, λ2, λ4. Since phages are plated at high density, the positive plaques are purified thrice by plating them at a low density and repeating the complete procedure of replica plating, hybridization and picking of positive plaques.

Example 4

Characterisation of the Lambda Clones

Example 4.1: Isolation of Lambda DNA

To isolate DNA from the recombinant clones, phages are first amplified. For this purpose *E. coli* LE392 host cells are grown to an optical density (600 nm) of 1.0 in LB-medium supplemented with 10 mM $MgSO_4$ and 0.2% maltose. Then 50 μl of the stocks of the purified phages are separately plated as described above. After an overnight incubation at 37° C. the phages are eluted from the nonconfluent plates by spreading 5 ml of SM over the plates and incubating for two hours with gentle shaking. The eluted phages are harvested and 0.1 ml chloroform is added. The mixture is briefly vortexed and cellular debris is removed by centrifugation. The supernatants are recovered, chloroform is added to 0.3% and the resulting plate lysate is stored at 4° C.

In order to obtain nearly confluent plates as starting material for the isolation of phage DNA, 10 ml portions of the plate lysates are plated with *E. coli* LE392 host cells. After overnight incubation at 37° C. the agarose top layer is scraped off from three nearly confluent plates. These layers are combined, 20 ml of SM and 0.4 ml of chloroform are added and the resulting mixture is shaken at 37° C. for 30 min. Cellular debris and agarose are removed by centrifugation, the supernatant is recovered and its volume adjusted to 18 ml with SM. An equal volume of 2M NaCl, 20% PEG6000 (BDH, Poole, GB) in SM is added and the solutions are mixed and placed on ice. After 75 min the phages are pelletted by centrifugation for 20 min at 1200×g at 4° C. The supernatant is decanted and the remaining fluid is removed with a Kleenex tissue. The pellet is resuspended in 3 ml SM and subsequently extracted with 3 ml of chloroform. The aqueous phase is treated with RNase A (67 μg/ml) and DNase I (33 μg/ml) for 20 min at 37° C. Then this mixture is extracted by adding 2 ml of phenol, vortexing, adding 1 ml of chloroform, vortexing again and separating the two phases by centrifugation. The aqueous phase is extracted twice more, with 3 ml of phenol/chloroform (1:1) and 3 ml of chloroform, respectively. Then the DNA is precipitated from the aqueous phase by the sequential addition of 0.3 ml 3M sodium acetate buffer (pH 5.2) and 6 ml of ethanol. This mixture is left at 4° C. for 16 h and then the DNA is recovered by centrifugation (10 min, 12000×g, 4° C.). The pellet is dissolved in 0.4 ml of TE buffer, RNase A is added to 200 μg/ml, and incubated at 37° C. for 1 h. The DNA is precipitated, by the addition of 38 μl 3M sodium acetate buffer (pH 5.2) and 0.8 ml ethanol at 4° C. for 1 h. The DNA is recovered by centrifugation and subsequently dissolved 100 μl of TE.

Example 4.2: Restriction Analysis of the *A. niger* N400 pepE Clones

It is established by restriction analysis that all three phages contain inserts which are derived from the same region of the *A. niger* genome and a partial restriction map of λ1 is constructed.

2 μg of phage DNA is digested with 20 units of BamHI in a volume of 20 μl for 1 h at 37° C. in the buffer recommended by the supplier (BRL) and then heated at 65° C. for 10 min. The samples are run on a 0.7% agarose gel and photographed. The DNA is transferred to nitrocellulose membrane and hybridized with the labelled *N. crassa* pep4 probe. It is clear from these digests that all three phages are identical and that a 5.8 kb fragment is the only fragment that hybridises to the pep4 probe and hence contains most if not all of the corresponding *A. niger* gene. One of the three identical phages is named λ1 and is chosen for further experiments.

Example 5

Cloning of PEPE into a Plasmid and its Sequencing and Characterisation

Example 5.1: Construction of pPEPE

λ1 DNA is incubated with the restriction enzyme BamHI, essentially as described above. Following extraction with chloroform, the DNA is precipitated, pelletted by centrifugation, dissolved in sample buffer and subjected to electrophoresis on a 0.6% agarose gel in 1×TBE buffer. A gel slice containing the 5.8 kbp BamHI fragment is recovered and the DNA is electroeluted. This is then extracted with 100 μl of chloroform and ethanol precipitated and redissolved in 40 ml of TE buffer. The DNA concentration is estimated by agarose gel electrophoresis followed by visualisation of the band under UV light.

pTZ18R vector is prepared by digestion with BamHI, under the conditions recommended by the supplier (BRL). The DNA is extracted with phenol, phenol/chloroform (1:1) and chloroform and the DNA ethanol precipitated.

100 ng of each of the above fragments are ligated together in a reaction volume of 25 μl, containing the buffer recommended by BRL plus ATP (1 mM), 1.5 U of T4 DNA ligase (BRL). The reaction mixture is incubated for 16 h at 16° C. and then used to transform *E. coli* DH5αF'. The cells are plated on LB agar plates containing 25 μg/ml ampicillin, 0.005% Xgal, 0.05 mM IPTG and incubated overnight at 37° C.

Several single white colonies are used to prepare overnight cultures in LB medium supplemented with 0.1% glucose and 25 mg/ml ampicillin. These cultures are used to isolate plasmid, using the miniprep method of Holmes and Quigley [Holmes, D. S. and Quigley, M., Anal. Biochem. 114:193(1981)]. The plasmids are digested with several restriction enzymes, according to the recommendations of the supplier (BRL) and in the presence of RNase A (0.5 mg/ml), and the products are analyzed on an agarose gel. Plasmids that give rise to BamHI fragments of the expected size are selected and the *E. coli* cells harbouring them are kept on glycerol at −20° C. This plasmid is called pPEPE (deposited with the DSM).

Example 5.2: Nucleotide Sequence of pepE

The pepE subclone, a 5.8 kbp BamHI fragment in the pTZ18R vector, is partially sequenced by the dideoxy-chain termination method [Sanger et al., Proc. Natl. Acad. Sci. U.S.A. 74:5463–67(1977)] using synthetic oligonucleotide primers and Sequenase (United States Biochemical Corp.).

The complete nucleotide sequence is present in the Sequence Listing. The open reading frame is identified by comparison to other known aspartic proteases and this is confirmed by transcription mapping.

Example 5.3: RNA Mapping of PEPE

Total RNA is prepared from ground freeze dried mycelia that is grown on minimal media with glucose as carbon source and ammonia as nitrogen source by the method of Frederick and Kinsey [Curr. Genet. 18:53–58(1990)]. The 5' end of the messenger RNA is identified by hybridising total RNA with 32-P end labelled oligonucleotide A (SEQ ID NO. 12) and sizing the runoff transcript produced by reverse transcriptase on a sequencing gel by comparison to sequencing reactions produced by dideoxy sequencing with the same oligonucleotide (Maniatis et al., Molecular Cloning. A Laboratory Manual. Cold Spring Harbor Laboratory, Cold Spring Harbor, N.Y., 1982). The precise splice sites of the introns are identified by cloning and sequencing partial cDNA copies of the pepE message. First strand synthesis is performed by standard methods (Maniatis et al., op. cit.) except the priming oligonucleotide is either oligonucleotide C (SEQ ID NO. 14) or oligonucleotide E (SEQ ID NO. 16). These cDNAs are subjected to PCR using oligonucleotides B (SEQ ID NO. 13) and C or oligonucleotides D (SEQ ID NO. 15) and E cloned into pTZ18R. Both strands of two independent clones of each are completely sequenced. The total length of the mRNA produced by the pepE gene is determined by Northern analysis using the 2.8 kb BamHI-BglII fragment as probe (Maniatis et al., op. cit) and is determined to be between 1.3 and 1.5 kb which corresponds to that expected from the size of the open reading frame and position of the transcription start site.

Example 6

Genomic Disruption of PEPE

Example 6.1: Construction of pTZ18REE pTZ18R is cut at the unique HindIII site, which is filled in with T4 polymerase, and ligated in the presence of an excess of unphosphorylated EcoRI linkers having the sequence 5'GGAATTCC. Upon transformation into *E. coli* a plasmid pTZ18REE is generated which has two EcoRI sites, one at each end of the polylinker sequence. The correct plasmid is identified by sequencing.

Example 6.2: Construction of pPEPEPYRA

The 4 kb XbaI fragment containing the pyrA gene is excised from pAXI and purified from the vector sequences. The fragment is treated with T4 polymerase to fill in the sticky ends, phenol extracted and ethanol precipitated.

pPEPE is cut with EcoRI, dephosphorylated with bacterial alkaline phosphatase, treated with T4 polymerase to fill in the 5' overhangs and then cut with BamHI. The fragments are separated on an agarose gel and the 3.4 kb EcoRI(blunt)-BamHI fragment is purified.

pPEPE is cut with HindIII, dephosphorylated with bacterial alkaline phosphatase, treated with T4 polymerase to fill in the 5' overhangs and then cut with BamHI. The fragments are separated on an agarose gel and the 1.4 kb HindIII(blunt)-BamHI fragment is purified.

pTZ18R is cut with BamHI and dephosphorylated with bacterial alkaline phosphatase.

The four above fragments are ligated together. After transformation of *E. coli*, the colonies carrying the correct plasmids are identified by restriction digest of mini-plasmid preparations.

pPEPEPYRA consists of pTZ18R vector containing on EcoRI fragment which carries the PEPE gene, which has the central EcoRI-HindIII and EcoRI-EcoRI fragments, which include most of the mature protease open reading frame, replaced by an XbaI DNA fragment encoding orotidine monophosphate decarboxylase.

Example 6.4: Transformation of *A. niger*

10 μg of plasmid pPEPEPYRA is digested to completion by EcoRI. The completeness of the digest is checked by running an aliquot on a gel and the remainder of the DNA is phenol extracted, ethanol precipitated and resuspended in 20 μl of sterile water.

Conidial spores of auxotrophic *A. niger* An8 (DSM 3917) are grown for 4 days at 28° C. on complete medium until fully sporulated. $2 \times 10^8$ conidiospores are used to inoculate 200 ml of minimal medium supplemented with 1 g/l arginine and uridine.

After 20 hours growth at 28° C. at 180 rpm the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm) until sufficient protoplasts are released (detected microscopically after 90–120 min). The protoplast suspension is filtered through a glass wool plug in a funnel to remove mycelial debris. The protoplasts are pelleted by mild centrifugation (10 min, 2000 rpm) at room temperature and washed twice with 10 ml 0.8M KCl, 50 mM $CaCl_2$. The protoplasts are finally resuspended in 200–500 μl 0.8M KCl, 50 mM $CaCl_2$ to give a concentration of $1 \times 10^8$ spheroplasts per ml.

For transformation a 200 μl aliquot of the protoplast suspension is incubated with 5 μg of the EcoRI digested pPEPEPYRA 50 μl PCT (10 mM Tris-HCl pH 7.5, 50 mM $CaCl_2$, 25% PEG 6000). The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with liquid minimal agar medium (Minimal medium+1 g/l arginine+10 g/l Bacto-Agar (Difco)), stabilised with 0.8M KCl. The mixtures are immediately poured on agar plates of the same medium and incubated at 30° C.

After 2–3 days of growth at 28° C., stable transformants appear as vigorously growing and sporulating colonies on a background growth of many hundred small, presumably abortive, transformants.

Example 6.5: Identification of Gene Disruptions

From the stable colonies, individual spore suspensions are made and streaked on fresh minimal plus arginine plates. Single colonies are selected and restreaked to give pure cultures. These are used to inoculate 200 ml of liquid minimal media supplemented with 1 g/l arginine. After 24 h at 30° C. shaling at 180 rpm, the mycelia is harvested on filter paper and the pad freeze dried. After drying DNA is prepared from the individual pads by grinding the pads to a fine powder with a pestle and mortar. 60 mg of this powder is resuspended in 3 ml of 1% Sodium dodecylsulfate, 0.1% Tween 80, 1M ammonium acetate by vortexing. This is heated at 65° C. for 20 min with occasional mixing. The cell debris is separated from the DNA solution by centrifugation at 15,000 rpm for 5 min. The supernatant is extracted twice with phenol, twice with chloroform and ethanol precipitated. The DNA pellet is reddisolved in 100 μl of sterile TE.

20 μl of each DNA is digested with EcoRI in the presence of 1 μg of RNAaseA for 1 h. This is separated on an agarose gel and transferred to nitrocellulose membrane and baked. The BglII-HindIII fragment from pPEPE containing the PEPE gene is purified, labelled by nick translation and used to probe the filters. Strains which carry a disruption of the pepE gene are easily recognized by lacking the 0.5 kb EcoRI hybridising fragment as well as having altered mobility of the other two flanking fragments.

One of these strains is plated on media containing uridine and 5-fluoro-orotic acid. Mutants to pyrimidine auxotrophy are identified by the stronger growth on this media and are picked off and purified by streaking for single colonies.

Example 6.6: Production of Interferon in pepE⁻ *A. niger* Strain

One of the pepE⁻ *A. niger* An8 strains isolated in Example 6.5 is used as a host for subsequent transformation with pyrA⁺ containing plasmids and expression cassettes containing a heterologous gene for interferon.

Conidial spores of the uridine auxotrophic pepE⁻ mutant of *A. niger* An8 are grown for 4 days at 28° C. in complete medium until fully sporulated. $2 \times 10^8$ conidiospores are used to inoculate 200 ml minimal medium supplemented 1 g/l arginine and uridine.

After 20 hours growth at 28° C. and 180 rpm, the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm.) until sufficient protoplasts are released (detected microscopically after 90–120 min). The protoplast suspension is filtered through a glass wool plug in a funnel to remove mycelial debris. The protoplasts are pelleted by mild centrifugation (10 min, 2000 rpm) at room temperature and washed twice with 10 ml 0.8M KCl, 50 mM $CaCl_2$. The protoplasts are finally resuspended in 200–500 μl 0.8M KCl, 50 mM $CaCl_2$ to give a concentration of $1 \times 10^8$/ml.

For transformation a 200 μl aliquot of the protoplast suspension is incubated with 5 μg of pAXI (DSM 7017) and 50 μg pGIIss-IFN AM119 or pGII-IFN AM119 DNA (both plasmids are fully disclosed in EP-Application 0 421 919) ,50 μl PCF (10 mM Tris-HCl pH 7.5, 50 mM $CaCl_2$, 25% PEG 6000). The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with liquified minimal agar medium (Minimal medium +1 g/l arginine+10 g/l Bacto-Agar (Difco)), stabilised with 0.8M KCl. The mixtures are immediately poured on agar plates of the same medium and incubated at 30° C.

After 2–3 days of growth at 28° C., stable transformants appear as vigorously growing and sporulating colonies on a background growth of many hundred small, presumably abortive, transformants.

Transformants are picked and analysed for interferon expression. Interferon activity is determined according to the procedure of Armstrong (J. A. Armstrong, Appl. Microbiol. 21, 732 (1971)) using human CCL-23 cells and vesicular stomatitis virus (VSV) as the challenge virus.

Conidial spores from transformants are individually precultured into 50 ml of a preculture medium (Pectin Slow Set L (Unipectin, SA, Redon, France) 3 g/l, $NH_4Cl$ 2 g/l, $KH_2PO_4$ 0.5 g/l, NaCl 0.5 g/l, $Mg_2SO_4 \cdot 7H_2O$ 0.5 g/l, $Ca_2SO_4 \cdot 2H_2O$ 0.5 g/l, pH 7.0, 1% arginine). The preculture is incubated for 72 hours at 250 rpm and 28° C. 10% of the preculture is used to inoculate 50 ml of main culture medium (Soybean fluor 20 g/l, pectin Slow Set 5 g/l, 1% arginine). The culture is grown up for 72–96 hours at 250 rpm and 28° C.

At various times (every 20 hours) samples are taken, the cells are pelleted by centrifugation and broken by freezedrying and dry grinding. Supernatant and cell extracts are both tested for inteferon activity as described (supra). The bulk of the interferon activity is found secreted into the medium in transformants carrying pGIIss-IFN AM119 while in transformants carrying pGII-IFN AM119 it is mainly in the cell extract.

Example 7

Overexpression of pepE in A. niger

Example 7.1: Overexpression of Multiple Copies

A. niger An8 is transformed with 1 μg pAXI plus 10 μg pPEPE to yield uridine prototrophs. Colonies are purified and DNA prepared as described above. Southern blots using the BglII-HindIII fragment of pPEPE showed that some transformants have a single copy of pPEPE integrated into their genome whereas others have upto and above 10 extra copies in their genome. There strains produce correspondingly more proteolytic activity and are stable mitotically.

Example 7.2: Overexpression of pepE from Gene Fusions

The promoter of A. niger pyruvate kinase is amplified from pGW1100 (DSM 5747) by PCR technology using oligonucleotide 1 (SEQ ID NO. 3) and oligonucleotide 2 (SEQ ID NO. 4). The fragment is cut with BamHI and PstI and purified from an agarose gel.

The Aspergillus-aspartic proteinase coding region is amplified from pPEPE by PCR technology using oligonucleotide 3 (SEQ ID NO. 5) and oligonucleotide 4 (SEQ ID NO. 6). The fragment is cut with PstI and XhoI and purified from an agarose gel.

The terminator of A. niger pyruvate kinase is amplified from PGW1100 (DSM 5747) by PCR technology using oligonucleotide 5 (SEQ ID NO. 7) and oligonucleotide 6 (SEQ ID NO. 8). The fragment is cut with BamHI and PstI and purified from an agarose gel.

pTZ18R is cut with BamHI and dephosphorylated with bacterial alkaline phosphatase.

Ligation of the four fragments above and transformation of E. coli leads to the formation of plasmid pPKIPEPE who's correct structure is confirmed by restriction digestion and sequencing. pPKIPEPE contains a BamHI fragment inserted into pTZ18R, which fragment contains an expression cassette consisting of the pyruvate kinase promoter of A. niger fused to the ATG start codon of the pepE gene of A. niger, which is terminated by the pyruvate kinase terminator. pPKIPEPE is used with pAXI to cotransform A. niger An8 to uridine prototrophy.

The presence of the pki-pepE fusion is confirmed by making DNA from individual purified transformrants and using it for Southern analysis using probes from pki and pepE. Strains with one or more copy of this gene fusion integrated into their genome are shown to produce more proteolytic activity when the cells are grown rapidly on glucose as C source.

Example 8: Expression of pepE in Other Organisms: Expression in Yeast

The plasmid pPEPE is in vitro mutagenised with the three synthetic oligonucleotides shown in the sequence listing as oligonucleotide 7, 8 and 9 under SEQ ID NO. 9, 10 and 11, respectively, which loop out all of the three introns. This creates a plasmid pPEPEI who's sequence is confirmed by complete sequencing of the open reading frame.

pFBY129 (deposited as DSM 7016) is cut with EcoRI and treated with S1 nuclease to remove the sticky ends. This blunt ended molecule is religated with an excess of unphosphorylated linkers of the sequence 5'CCTGCAGG and transformed into E. coli. The correct plasmid with a PstI site replacing the EcoRI site is identified by sequencing and is called pFBY129P.

pFBY25 (DSM 7020) is cut with SnaBI and treated with T4 polymerase to fill in the ends. This blunt ended molecule is religated with an excess of unphosphorylated linkers of the sequence 5'GAGATCTC and transformed into E. coli. The correct plasmid with a BglII site replacing the SnaBI site is identified by restriction analysis of plasmid minipreparations and is confirmed by sequencing. This plasmid is called pFBY25Bg. pFBY25Bg is digested with BglII and dephosphorylated with bacterial alkaline phosphatase.

A fragment is amplified by PCR from pPEPEI using oligonucleotides 3 and 4. This fragment containing the whole pepE open reading frame without introns is cut with PstI and XhoI and purified from an agarose gel.

The terminator of the A. niger pyruvate kinase gene is amplified from PGW1100 (DSM 5747) by PCR using oligonucleotides 5 and 6. The fragment is cut with SalI and BamHI and purified from an agarose gel.

The Gal10 yeast promoter is excised from pFBY129P with BamHI and PstI and the fragment is purified from an agarose gel.

The three fragments obtained above are ligated together with the BglII-digested and dephosphorylated pFBY25Bg to yield plasmid pGALPEPE. The correct structure is confirmed by restriction analysis. The plasmid PGALPEPE is transformed into yeast and the transformants are shown to produce PEPE protein after induction of the expression of the recombinant gene with galactose.

Deposition of Microorganisms

Following microorganisms are deposited under the Budapest treaty with the Deutsche Sammlung von Mikroorganismen und Zellkulturen, Mascheroder Weg 1b, D-38124 Braunschweig:

| Microorganism/Plasmid | Depos. Date | Deposition No. |
| --- | --- | --- |
| E. coli DHScaF'/pGW1100 | Jan. 18, 1990 | DSM 5747 |
| A. niger An8 | Dec. 11, 1986 | DSM 3917 |
| E. coli DHScaF'/pFBY129 | March 30, 1992 | DSM 7016 |
| E. coli DHScaF'/pAXI | March 30, 1992 | DSM 7017 |
| E. coli DHScaF'/pFBY25 | March 30, 1992 | DSM 7020 |
| E. coli DHScaF'/pPEPE | Oct. 7, 1993 | DSM 8613 |
| E. coli BB4/pNCPEP4 | Oct. 7, 1993 | DSM 8612 |

We claim:

1. A process for the preparation of a DNA molecule encoding an *Aspergillus niger* vacuolar aspartic protease having the amino acid sequence shown in SEQ ID NO:2, comprising culturing a host cell transformed with the DNA molecule and isolating the DNA molecule from the host cell.

2. A substantially pure *Aspergillus niger* vacuolar aspartic protease having the same aspartic protease activity as the protease having the amino acid sequence shown in SEQ ID NO:2.

3. A substantially pure *Aspergillus niger* vacuolar aspartic protease having the amino acid sequence shown in SEQ ID NO:2.

* * * * *

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 2875 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: pepE
        ( B ) STRAIN: Aspergillus niger N400

( i x ) FEATURE:
        ( A ) NAME/KEY: CDS
        ( B ) LOCATION: join(1269..1370, 1462..1612, 1669..2323, 2382
            ..2667)
        ( D ) OTHER INFORMATION: /function="Aspartic Protease"
            / product= "PEPE"
            / gene= "pepE"

( i x ) FEATURE:
        ( A ) NAME/KEY: intron
        ( B ) LOCATION: order(1371..1461, 1613..1668, 2324..2381)

( i x ) FEATURE:
        ( A ) NAME/KEY: exon
        ( B ) LOCATION: join(1269..1370, 1462..1612, 1669..2323, 2382
            ..2667)

( x i ) SEQUENCE DESCRIPTION: SEQ ID NO: 1:

```
GGATCCGGCC  TTGCTACGTC  CGGGTCGTTT  GGACCGGAAG  ATCGAGTTTC  CGTCTTTGCG      60
CGACCGGCGT  GAGCGCCGGT  TGATTTTCTC  TACGATAGCA  TCCAAGATGT  CGCTTTCGCC     120
GGAAGTTGAC  CTGGACTCGC  TGATTGTGCG  CAATGAGCCC  CTCTCGGGTG  CGGTCATTGC     180
CGCGATCATG  CAAGAGGCGG  GTCTCCGTGC  TGTCCGGAAG  AACCGTTACA  ACATCATCCC     240
TAGGTCTGAT  CTCGAGGATG  CTTACGCCGC  CCAGGTGAAG  ACCGGACAGG  AAGCGGATAG     300
GTACGGGACA  TTTTCTAATC  TACCCGCGAT  CGGGACATGG  CTAACCAAGC  ATATAGACTC     360
GAATTCTACC  GGTAAATCAA  GTATGGGACG  TGCATCAGGC  TGGATATCGG  ATTACGCAAG     420
GCGAACAGGG  GGACCGTTAG  CTGTATTATC  AACATCTAGG  CTATTTCATA  TTAGGACAAC     480
GACTGACGCA  TTGGGTATTC  CGCTGGGGTA  GTCTTATCGG  TTGGGGCCAA  GTACCTTGTA     540
GAACTGTAAC  CCACGTTAAT  ACCGCCACTT  GGCTGGGGCG  GTTATTTAGC  ATATGTAAGC     600
TCCAGTTGGA  CGGCTACCCG  AGCTTCCCAT  GATCTACAGG  AGTACGTGTC  TGGCTGTCTG     660
CTGCCTACTT  GGTAGACAGG  TCAGCGATAG  GTAGATAGGA  CCTGTCCGCA  GCTGTTGGCT     720
AGTTTGGTAA  GGCGGTTGCG  CTAGTTTGAA  GTAGGCAGGC  ACCGGGAACC  TAAGGCGGTC     780
TTACATCATC  ACCCGCGCTC  GGATTCGCGT  GATCCGACCA  TCACGATAAG  GCCTCAGGTA     840
GCAAGGAGAC  CTTCCAGACA  GCTCTGAATG  AGACTCAAAG  GTAGATATAA  TGATGGAAAG     900
ATAGGATAGC  TAGATCAGGC  TTATTGTACC  TGATCGTTAA  GAGCCTAGAG  AAGATGTACC     960
TGGAAGACCT  GGCAGCTACA  ATCACCTGGA  GCGATAACCC  GTGACGATCC  CCTTGCCAAA    1020
TGACGCAGCC  GGGCTGGCCA  ACCATTGGCT  GCGACCTGGC  AGGTCCGTCC  GCAACCAGCG    1080
```

```
CCGCCCGGCT CCAAGTCACC CGCATCACTC TTCCCTACCC CCAGACCTCC TCTTTTCCCT     1140

TGCTATCCTC CATCTCTTCT TCATCGTTCT TTGTCTCTAT CATCATTTTC TATTCATACG     1200

TGCATCCTTC AGTCGTTTGG CCCAGTCCAT CATATCCCGC TGGGTAGCCG TTTCGCCGT      1260

CGCCCATC ATG AAA TCA GCC TCC TTG CTC ACA GCA TCC GTG CTG TTG GGC      1310
         Met Lys Ser Ala Ser Leu Leu Thr Ala Ser Val Leu Leu Gly
         1               5                       10

TGT GCC TCC GCC GAG GTT CAC AAG CTC AAG CTT AAC AAG GTG CCT CTG       1358
Cys Ala Ser Ala Glu Val His Lys Leu Lys Leu Asn Lys Val Pro Leu
15                  20                  25                  30

GAA GAG CAG CTT GTGAGTGTGG TCTTTCACTG CTTTTGTCTT TTTAGCTAGT           1410
Glu Glu Gln Leu

TAGCTTCAAA GAAGCTCCAG AACCATTCAA AGCTAATTTC GTGGCCTATA G TAC ACG      1467
                                                        Tyr Thr
                                                        35

CAT AAC ATC GAC GCC CAT GTC CGC GCT CTG GGC CAG AAG TAC ATG GGT       1515
His Asn Ile Asp Ala His Val Arg Ala Leu Gly Gln Lys Tyr Met Gly
        40              45                      50

ATC CGC CCG TCC ATC CAC AAA GAG CTG GTC GAG GAG AAC CCT ATC AAT       1563
Ile Arg Pro Ser Ile His Lys Glu Leu Val Glu Glu Asn Pro Ile Asn
55                  60                  65

GAC ATG AGC CGT CAT GAT GTT CTG GTG GAC AAC TTC CTG AAC GCA CAG  T    1612
Asp Met Ser Arg His Asp Val Leu Val Asp Asn Phe Leu Asn Ala Gln
70                  75                  80

GTATGGAGAT ACCATCTTCT TATGGCTGCA ACTACTGCTG ACCCTTCCTG CCATAG  AC     1670
                                                              Tyr
                                                              85

TTT TCT GAG ATC GAG CTG GGT ACT CCC CCC CAG AAG TTC AAG GTT GTC       1718
Phe Ser Glu Ile Glu Leu Gly Thr Pro Pro Gln Lys Phe Lys Val Val
            90                  95                      100

CTG GAC ACT GGC AGC TCG AAC CTT TGG GTT CCT TCG AGC GAA TGC AGC       1766
Leu Asp Thr Gly Ser Ser Asn Leu Trp Val Pro Ser Ser Glu Cys Ser
            105                 110                 115

TCT ATC GCT TGC TAC CTC CAC AAC AAG TAT GAT TCG TCT GCC TCC AGT       1814
Ser Ile Ala Cys Tyr Leu His Asn Lys Tyr Asp Ser Ser Ala Ser Ser
        120                 125                 130

ACG TAT CAC AAG AAT GGC AGT GAA TTC GCC ATC AAG TAC GGC TCT GGC       1862
Thr Tyr His Lys Asn Gly Ser Glu Phe Ala Ile Lys Tyr Gly Ser Gly
    135                 140                 145

AGC CTT AGC GGA TTC GTT TCT CAG GAC ACC CTG AAG ATT GGC GAC CTG       1910
Ser Leu Ser Gly Phe Val Ser Gln Asp Thr Leu Lys Ile Gly Asp Leu
150                 155                 160                 165

AAG GTC AAG GGA CAG GAC TTC GCT GAG GCG ACC AAT GAG CCT GGC CTT       1958
Lys Val Lys Gly Gln Asp Phe Ala Glu Ala Thr Asn Glu Pro Gly Leu
            170                 175                 180

GCC TTT GCC TTC GGC CGG TTC GAT GGC ATT CTC GGC TTG GGT TAT GAC       2006
Ala Phe Ala Phe Gly Arg Phe Asp Gly Ile Leu Gly Leu Gly Tyr Asp
185                 190                 195

ACC ATC TCC GTG AAC AAG ATT GTT CCT CCC TTC TAC AAC ATG CTT GAC       2054
Thr Ile Ser Val Asn Lys Ile Val Pro Pro Phe Tyr Asn Met Leu Asp
        200                 205                 210

CAG GGG CTC CTC GAC GAG CCG GTC TTT GCC TTC TAC CTT GGA GAC ACC       2102
Gln Gly Leu Leu Asp Glu Pro Val Phe Ala Phe Tyr Leu Gly Asp Thr
    215                 220                 225

AAC AAG GAG GGT GAC GAG TCC GTG GCG ACC TTC GGT GGT GTC GAC AAG       2150
Asn Lys Glu Gly Asp Glu Ser Val Ala Thr Phe Gly Gly Val Asp Lys
230                 235                 240                 245

GAC CAC TAC ACC GGC GAG CTG ATC AAG ATC CCC CTC CGG CGC AAG GCT       2198
Asp His Tyr Thr Gly Glu Leu Ile Lys Ile Pro Leu Arg Arg Lys Ala
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 250 |     |     |     |     | 255 |     |     |     |     | 260 |     |      |
| TAC | TGG | GAG | GTT | GAG | CTT | GAC | GCC | ATT | GCT | CTT | GGC | GAT | GAT | GTT | GCT | 2246 |
| Tyr | Trp | Glu | Val | Glu | Leu | Asp | Ala | Ile | Ala | Leu | Gly | Asp | Asp | Val | Ala |      |
|     |     |     | 265 |     |     |     |     | 270 |     |     |     |     | 275 |     |     |      |
| GAG | ATG | GAG | AAC | ACC | GGT | GTC | ATT | CTG | GAC | ACT | GGT | ACC | TCC | CTG | ATT | 2294 |
| Glu | Met | Glu | Asn | Thr | Gly | Val | Ile | Leu | Asp | Thr | Gly | Thr | Ser | Leu | Ile |      |
|     | 280 |     |     |     |     | 285 |     |     |     |     | 290 |     |     |     |     |      |
| GCT | CTG | CCT | GCT | GAC | CTG | GCT | GAG | ATG | AT  |     | GTAAGTCGAA | TTCCTCGGAT |     |     |     | 2343 |
| Ala | Leu | Pro | Ala | Asp | Leu | Ala | Glu | Met | Ile |     |     |     |     |     |     |      |
|     | 295 |     |     |     |     | 300 |     |     |     |     |     |     |     |     |     |      |

| | | | | |
|---|---|---|---|---|
| TCCTGGGTTG | AAAAGAAATG | CTGCTAACAA | CCTTCTAG C | AAT GCT CAG ATC GGT | 2397 |
| | | | | Asn Ala Gln Ile Gly |
| | | | | 305 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GCT | AAG | AAG | GGC | TGG | ACC | GGC | CAG | TAC | ACC | GTT | GAC | TGC | GAC | AAG | CGC | 2445 |
| Ala | Lys | Lys | Gly | Trp | Thr | Gly | Gln | Tyr | Thr | Val | Asp | Cys | Asp | Lys | Arg |      |
|     | 310 |     |     |     |     | 315 |     |     |     |     | 320 |     |     |     |     |      |
| TCG | TCC | CTG | CCC | GAT | GTT | ACT | TTC | ACC | CTT | GCC | GGC | CAC | AAC | TTC | ACC | 2493 |
| Ser | Ser | Leu | Pro | Asp | Val | Thr | Phe | Thr | Leu | Ala | Gly | His | Asn | Phe | Thr |      |
| 325 |     |     |     | 330 |     |     |     |     | 335 |     |     |     |     | 340 |     |      |
| ATC | TCA | TCG | TAT | GAC | TAC | ACC | TTG | GAG | GTG | CAG | GGC | TCT | TGC | GTC | AGT | 2541 |
| Ile | Ser | Ser | Tyr | Asp | Tyr | Thr | Leu | Glu | Val | Gln | Gly | Ser | Cys | Val | Ser |      |
|     |     |     | 345 |     |     |     |     | 350 |     |     |     |     | 355 |     |     |      |
| GCC | TTC | ATG | GGC | ATG | GAC | TTC | CCT | GAG | CCG | GTT | GGT | CCC | TTG | GCC | ATT | 2589 |
| Ala | Phe | Met | Gly | Met | Asp | Phe | Pro | Glu | Pro | Val | Gly | Pro | Leu | Ala | Ile |      |
|     |     |     | 360 |     |     |     |     | 365 |     |     |     |     | 370 |     |     |      |
| TTG | GGC | GAT | GCG | TTC | CTG | CGC | AAG | TGG | TAC | AGC | GTG | TAT | GAC | CTG | GGC | 2637 |
| Leu | Gly | Asp | Ala | Phe | Leu | Arg | Lys | Trp | Tyr | Ser | Val | Tyr | Asp | Leu | Gly |      |
|     |     | 375 |     |     |     |     | 380 |     |     |     |     | 385 |     |     |     |      |
| AAC | AGC | GCT | GTT | GGT | CTG | GCC | AAG | GCC | AAG | TAAATTAGTT | CTGCGGGTTG |     |     |     |     | 2687 |
| Asn | Ser | Ala | Val | Gly | Leu | Ala | Lys | Ala | Lys |     |     |     |     |     |     |      |
|     | 390 |     |     |     |     | 395 |     |     |     |     |     |     |     |     |     |      |

| | | | | | |
|---|---|---|---|---|---|
| ATGTGGTATC | TATGATGCAG | CTGTTGCTGT | CATTATTGCT | TCTTGTAGCT | TGATCTATGA | 2747 |
| TTTTTGCAGA | CGAACACACG | TGATGTTGTG | AATGGTCTCA | TGTTTGCAGC | GGTTGCCGGA | 2807 |
| TAGATTCTAG | GGATCTTCAA | TGGAAAGCCG | GTGATATTAT | TTGACATTTA | TTTGGGCACT | 2867 |
| GAAGATCT | | | | | | 2875 |

( 2 ) INFORMATION FOR SEQ ID NO: 2:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Met | Lys | Ser | Ala | Ser | Leu | Leu | Thr | Ala | Ser | Val | Leu | Leu | Gly | Cys | Ala |
| 1 | | | | 5 | | | | | 10 | | | | | 15 | |
| Ser | Ala | Glu | Val | His | Lys | Leu | Lys | Leu | Asn | Lys | Val | Pro | Leu | Glu | Glu |
| | | | 20 | | | | | 25 | | | | | 30 | | |
| Gln | Leu | Tyr | Thr | His | Asn | Ile | Asp | Ala | His | Val | Arg | Ala | Leu | Gly | Gln |
| | | | 35 | | | | | 40 | | | | | 45 | | |
| Lys | Tyr | Met | Gly | Ile | Arg | Pro | Ser | Ile | His | Lys | Glu | Leu | Val | Glu | Glu |
| | 50 | | | | | 55 | | | | | 60 | | | | |
| Asn | Pro | Ile | Asn | Asp | Met | Ser | Arg | His | Asp | Val | Leu | Val | Asp | Asn | Phe |
| 65 | | | | | 70 | | | | | 75 | | | | | 80 |
| Leu | Asn | Ala | Gln | Tyr | Phe | Ser | Glu | Ile | Glu | Leu | Gly | Thr | Pro | Pro | Gln |
| | | | | 85 | | | | | 90 | | | | | 95 | |

```
Lys  Phe  Lys  Val  Val  Leu  Asp  Thr  Gly  Ser  Ser  Asn  Leu  Trp  Val  Pro
               100                      105                      110

Ser  Ser  Glu  Cys  Ser  Ser  Ile  Ala  Cys  Tyr  Leu  His  Asn  Lys  Tyr  Asp
          115                      120                      125

Ser  Ser  Ala  Ser  Ser  Thr  Tyr  His  Lys  Asn  Gly  Ser  Glu  Phe  Ala  Ile
     130                      135                      140

Lys  Tyr  Gly  Ser  Gly  Ser  Leu  Ser  Gly  Phe  Val  Ser  Gln  Asp  Thr  Leu
145                      150                      155                           160

Lys  Ile  Gly  Asp  Leu  Lys  Val  Lys  Gly  Gln  Asp  Phe  Ala  Glu  Ala  Thr
                    165                      170                           175

Asn  Glu  Pro  Gly  Leu  Ala  Phe  Ala  Phe  Gly  Arg  Phe  Asp  Gly  Ile  Leu
               180                      185                           190

Gly  Leu  Gly  Tyr  Asp  Thr  Ile  Ser  Val  Asn  Lys  Ile  Val  Pro  Pro  Phe
          195                      200                      205

Tyr  Asn  Met  Leu  Asp  Gln  Gly  Leu  Leu  Asp  Glu  Pro  Val  Phe  Ala  Phe
     210                      215                      220

Tyr  Leu  Gly  Asp  Thr  Asn  Lys  Glu  Gly  Asp  Glu  Ser  Val  Ala  Thr  Phe
225                      230                      235                           240

Gly  Gly  Val  Asp  Lys  Asp  His  Tyr  Thr  Gly  Glu  Leu  Ile  Lys  Ile  Pro
               245                      250                      255

Leu  Arg  Arg  Lys  Ala  Tyr  Trp  Glu  Val  Glu  Leu  Asp  Ala  Ile  Ala  Leu
               260                      265                      270

Gly  Asp  Asp  Val  Ala  Glu  Met  Glu  Asn  Thr  Gly  Val  Ile  Leu  Asp  Thr
          275                      280                      285

Gly  Thr  Ser  Leu  Ile  Ala  Leu  Pro  Ala  Asp  Leu  Ala  Glu  Met  Ile  Asn
     290                      295                      300

Ala  Gln  Ile  Gly  Ala  Lys  Lys  Gly  Trp  Thr  Gly  Gln  Tyr  Thr  Val  Asp
305                      310                      315                           320

Cys  Asp  Lys  Arg  Ser  Ser  Leu  Pro  Asp  Val  Thr  Phe  Thr  Leu  Ala  Gly
                    325                      330                      335

His  Asn  Phe  Thr  Ile  Ser  Ser  Tyr  Asp  Tyr  Thr  Leu  Glu  Val  Gln  Gly
               340                      345                      350

Ser  Cys  Val  Ser  Ala  Phe  Met  Gly  Met  Asp  Phe  Pro  Glu  Pro  Val  Gly
          355                      360                      365

Pro  Leu  Ala  Ile  Leu  Gly  Asp  Ala  Phe  Leu  Arg  Lys  Trp  Tyr  Ser  Val
     370                      375                      380

Tyr  Asp  Leu  Gly  Asn  Ser  Ala  Val  Gly  Leu  Ala  Lys  Ala  Lys
385                      390                      395
```

( 2 ) INFORMATION FOR SEQ ID NO: 3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..18
        ( D ) OTHER INFORMATION: /standard_name= "oligonucleotide 1"

( x i ) SEQUENCE DESCRIPTION: SEQ ID NO: 3:

CCGACCTCGC TAGGAGAG                         18

( 2 ) INFORMATION FOR SEQ ID NO: 4:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..30
    ( D ) OTHER INFORMATION: /standard_name= "oligonucleotide 2"

( x i ) SEQUENCE DESCRIPTION: SEQ ID NO: 4:

GCAGCTGCAG TGATTGATCT CTACTGAACC    30

( 2 ) INFORMATION FOR SEQ ID NO: 5:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..30
    ( D ) OTHER INFORMATION: /standard_name= "oligonucleotide 3"

( x i ) SEQUENCE DESCRIPTION: SEQ ID NO: 5:

CCGCCTGCAG CCATCATGAA ATCAGCCTCC    30

( 2 ) INFORMATION FOR SEQ ID NO: 6:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..30
    ( D ) OTHER INFORMATION: /standard_name= "oligonucleotide 4"

( x i ) SEQUENCE DESCRIPTION: SEQ ID NO: 6:

CAGACTCGAG TTACTTGGCC TTGGCCAGAC    30

( 2 ) INFORMATION FOR SEQ ID NO: 7:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..28
    ( D ) OTHER INFORMATION: /standard_name= "oligonucleotide 5"

( x i ) SEQUENCE DESCRIPTION: SEQ ID NO: 7:

GCTAGTCGAC ATGCAAAAGC AGTCTGGC    28

( 2 ) INFORMATION FOR SEQ ID NO: 8:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..28
    ( D ) OTHER INFORMATION: /standard_name= "oligonucleotide 6"

( x i ) SEQUENCE DESCRIPTION: SEQ ID NO: 8:

CGATGGATCC TGATCCTCAA GGGATTCG         28

( 2 ) INFORMATION FOR SEQ ID NO: 9:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..36
    ( D ) OTHER INFORMATION: /standard_name= "oligonucleotide 7"

( x i ) SEQUENCE DESCRIPTION: SEQ ID NO: 9:

CCTCTGGAAG AGCAGCTTTA CACGCATAAC ATCGAC     36

( 2 ) INFORMATION FOR SEQ ID NO: 10:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..38
    ( D ) OTHER INFORMATION: /standard_name= "oligonucleotide 8"

( x i ) SEQUENCE DESCRIPTION: SEQ ID NO: 10:

CAACTTCCTG AACGCACAGT ACTTTCTGA GATCGAGC     38

( 2 ) INFORMATION FOR SEQ ID NO: 11:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..38
    ( D ) OTHER INFORMATION: /standard_name= "oligonucleotide 9"

( x i ) SEQUENCE DESCRIPTION: SEQ ID NO: 11:

GCTGACCTGG CTGAGATGAT CAATGCTCAG ATCGGTGC    38

( 2 ) INFORMATION FOR SEQ ID NO: 12:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..30
    ( D ) OTHER INFORMATION: /standard_name= "oligonucleotide A"

( x i ) SEQUENCE DESCRIPTION: SEQ ID NO: 12:

CAACAGCACG GATGCTGTGA GCAAGGAGGC      30

( 2 ) INFORMATION FOR SEQ ID NO: 13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /standard_name= "oligonucleotide B"

( x i ) SEQUENCE DESCRIPTION: SEQ ID NO: 13:

GGGCTGTGCC TCCGCCGAGG      20

( 2 ) INFORMATION FOR SEQ ID NO: 14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /standard_name= "oligonucleotide C"

( x i ) SEQUENCE DESCRIPTION: SEQ ID NO: 14:

TAAGGCTGCC AGAGCCGTAC      20

( 2 ) INFORMATION FOR SEQ ID NO: 15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /standard_name= "oligonucleotide D"

( x i ) SEQUENCE DESCRIPTION: SEQ ID NO: 15:

CGGTGTCATT CTGGACACTG      20

( 2 ) INFORMATION FOR SEQ ID NO: 16:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..20
    ( D ) OTHER INFORMATION: /standard_name= "oligonucleotide E"

( x i ) SEQUENCE DESCRIPTION: SEQ ID NO: 16:

AGTAACATCG GGCAGGGACG 20